(12) United States Patent
Mosquera et al.

(10) Patent No.: US 12,353,683 B2
(45) Date of Patent: Jul. 8, 2025

(54) PROCESSING IRREGULAR GLUCOSE DATA USING DYNAMIC TIME WARPING

(71) Applicant: UnitedHealth Group Incorporated, Minnetonka, MN (US)

(72) Inventors: Javier Mosquera, Minnetonka, MN (US); Yinglong Guo, Minnetonka, MN (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 390 days.

(21) Appl. No.: 17/754,033

(22) PCT Filed: Nov. 26, 2019

(86) PCT No.: PCT/US2019/063394
§ 371 (c)(1),
(2) Date: Mar. 22, 2022

(87) PCT Pub. No.: WO2021/107938
PCT Pub. Date: Jun. 3, 2021

(65) Prior Publication Data
US 2022/0384000 A1  Dec. 1, 2022

(51) Int. Cl.
*G06F 3/0484* (2022.01)
*G06T 19/00* (2011.01)
(Continued)

(52) U.S. Cl.
CPC ............ *G06F 3/0484* (2013.01); *G06T 19/00* (2013.01); *G16H 15/00* (2018.01); *G16H 50/00* (2018.01); *G16H 50/70* (2018.01)

(58) Field of Classification Search
None
See application file for complete search history.

(56) References Cited

U.S. PATENT DOCUMENTS

| 2020/0149998 A1* | 5/2020 | Ayyagari | G06N 3/088 |
| 2023/0014068 A1* | 1/2023 | Ayoub | G06F 3/017 |

FOREIGN PATENT DOCUMENTS

| WO | WO-2020037055 A1 * | 2/2020 | E06B 3/6722 |

OTHER PUBLICATIONS

Cuturi, Marco et al. "Soft-DTW: A Differentiable Loss Function For Time-Series," arXiv preprint arXiv: 1703.01541v2 [stat.ML] Feb. 20, 2018, (23 pages).

(Continued)

*Primary Examiner* — Jwalant Amin
(74) *Attorney, Agent, or Firm* — Alston & Bird LLP

(57) ABSTRACT

Systems, methods, and computer-readable media determine a representative series using multiple time series of glucose readings. Systems may comprise one or more processors ("processing") and one or more computer-readable data storages (CRDS) storing instructions that, when executed by processing, cause processing to perform steps of the method. Some embodiments include one or more CRDS storing instructions for the methods that may be executed by one or more processors. Methods may comprise one or more processors receiving multiple time series in which each of the time series comprises glucose readings associated with respective timestamps. The time series may be generated during respective time periods. The one or more processors may adaptively determine a gamma parameter and determine a barycenter using the multiple time series and the gamma parameter. The one or more processors may apply a smoothing function to the barycenter yielding the representative series.

23 Claims, 16 Drawing Sheets

(51) Int. Cl.
    *G16H 15/00*       (2018.01)
    *G16H 50/00*       (2018.01)
    *G16H 50/70*       (2018.01)

(56) References Cited

OTHER PUBLICATIONS

International Searching Authority, International Search Report and Written Opinion for International Application No. PCT/US2019/063394, dated Aug. 13, 2020, (14 pages), European Patent Office, Rijswijk, Netherlands.

Turksoy, Kamuran et al. "Monitoring and Fault Detection of Continuous Glucose Sensor Measurements," 2015 American Control Conference, Palmer House Hilton, Jul. 1-3, 2015, pp. 5091-5096, Chicago, IL, USA.

Cuturi, Marco et al. "Soft-DTW: A Differentiable Loss Function For Time-Series," arXiv preprint arXiv: 1703.01541v2 [stat.ML] Feb. 20, 2018, (23 pages).

\* cited by examiner

PROCESSING IRREGULAR GLUCOSE DATA USING DYNAMIC TIME WARPING

CROSS REFERENCE TO RELATED APPLICATIONS

This application is a National Stage Application, filed under 35 U.S.C. § 371, of International Application No. PCT/US2019/063394, filed Nov. 26, 2019; the contents of which are hereby incorporated by reference in their entirety.

TECHNICAL FIELD

The present disclosure relates to the processing and visualization of glucose concentration data for improved clinical utility.

BACKGROUND

The advent of continuous glucose monitoring (CGM) has made the collection of frequent glucose concentration data dramatically more practical than it had been. In recent years, CGM devices (also referred to herein as CGM) have become less expensive, more accurate, and more prevalent. With respect to CGM, continuous does not require that readings be instantaneous or absolutely continuous. Some CGM devices use a small, disposable sensor inserted just under the skin. In microdialysis-based CGM, sensors may measure glucose in interstitial fluid. The glucose levels in the interstitial fluid may lag five or more minutes behind blood glucose levels. Other CGM devices may use non-invasive techniques such as transmission and reflection spectroscopy. CGM typically provides measurements every five to ten minutes, though frequency varies widely.

Glucose readings from CGM are often presented in graphs in which the vertical axis represents glucose concentration and the horizontal axis represents time and spans a period of 24 hours. Glucose readings from multiple days are superimposed over one another in an entrywise fashion. This entrywise comparison of 24-hour periods may reveal patterns in glucose concentration only if the daily activities affecting glucose levels of an individual occur on a very regular basis. As a non-limiting example, a person who eats meals, consumes medications, and exercises at the same times every day could readily determine the change in glucose concentration caused by these glucose-altering activities. Measures of central tendency (e.g. means and medians) could provide insight into glucose levels on a typical day and percentile measurements (e.g. 75th, 90th) could provide estimates of day-to-day variation.

However, the timing of glucose-altering activities for many individuals varies substantially. As a non-limiting example, the times at which a person eats a given meal can vary greatly from day to day and the number of meals eaten may vary as well. Many people consume snacks or sugary drinks between meals. Because regions of elevated or depressed glucose may be superimposed on baseline glucose readings, entrywise comparison of daily glucose readings may mask the effects of both glucose-altering behaviors and the true baseline glucose concentration.

FIG. 1 presents a graph of multiple 24-hour glucose time series superimposed in an entrywise fashion (100). The horizontal (x) axis (101) represents time of day over a 24-hour period. The vertical (v) axis (102) represents estimated glucose value (EGV) as glucose concentration in milligrams per deciliter. The pale, dashed curves (e.g. 111, 112, 113) on the plot are glucose time series for respective days. A point on the graph represents EGV at a particular time of day. The red curve (120) represents the $50^{th}$ percentile curve (also known as the median curve): at a given time of day, 50% of the glucose values generated at that time are less than the median. The two blue curves (131, 132) represent the $25^{th}$ and $75^{th}$ percentile curves, respectively. The two green curves (141, 142) represent the $10^{th}$ and $90^{th}$ percentile curves, respectively. In FIG. 1, EGV rose as high as 250 mg/dl on one occasion and exceeded 225 mg/dl on two additional occasions. However, even the $90^{th}$ percentile curve does not exceed 200 mg/dl. One reason for the failure of percentile curves to reflect extreme glucose readings may be that irregular patterns in eating and other glucose-altering behaviors cause higher glucose readings to be aggregated with lower readings when the readings are superimposed in an entrywise fashion.

Named meals are non-limiting examples of semantic events-events that are meaningful in terms of patterns of human behavior if not physiology. Primary determinants of a glucose levels may include the quantity, composition, and timing of consumed foods. Whether the consumption of those foods is called lunch, tea, or an afternoon snack is not physiologically relevant. However, physiological measures may follow patterns that coincide with repeating semantic events. As a non-limiting example, glucose levels may spike higher after breakfasts than for other meals due to the cultural tendency for breakfasts to have a high content of short-chain carbohydrates. Thus, while organizing data to observe patterns corresponding to semantic events may be difficult, there can be value in searching for such semantic patterns.

In addition to its use as a format for visual data presentation, entrywise grouping of glucose readings has been used as a method for analyzing data. As a data analysis method, entrywise comparison may be used to estimate measurements such as baseline glucose levels and typical glucose maxima following various meals. As with the entrywise visual presentation, entrywise calculations of the data may be influenced by daily glucose-altering events that do not occur at exactly the same time every day.

SUMMARY

Systems, methods, and computer-readable media described herein determine a representative series of multiple time series of glucose readings. Systems may comprise one or more processors and one or more computer-readable data storages (CRDS) storing instructions that, when executed by the one or more processors, cause the one or more processors to perform steps of the method. Some embodiments comprise one or more CRDS storing instructions for the methods that may be executed by one or more processors. Methods may comprise one or more processors receiving multiple time series in which each of the time series comprises glucose readings associated with respective timestamps. The time series may be generated during respective time periods. The one or more processors may adaptively determine a gamma parameter and determine a barycenter using the multiple time series and the gamma parameter. The one or more processors may apply a smoothing function to the barycenter yielding the representative series.

DETAILED DESCRIPTION

Method Embodiments

Methods described herein involve one or more processors (collectively "processing") determining a representative series using multiple glucose time series. The time series may comprise glucose readings corresponding to respective glucose concentrations and associated with respective timestamps. Timestamps may designate times or sequence position within each time series at which readings were generated. It is not essential that timestamps be accurate with respect to absolute time or timespans between time series. As a non-limiting example, if readings are generated at five-minute intervals and the time period of a time series starts at 5:00 PM on Sep. 27, 2019, the timestamp for a reading in the time period need not comprise information about the absolute time at which the reading was generated (e.g. 5:05 PM on Sep. 27, 2019). In some embodiments, timestamps may simply indicate an amount of time after the start time at which a reading was generated (e.g. that the reading was generated five minutes after the start time of the time series). In some embodiments, the timestamp may comprise or consist only of the sequence position of the reading (e.g. that the reading is the second reading in the time series).

In certain exemplary embodiments, the respective glucose time series may share a common duration. However, those familiar with the art will recognize that the glucose time series need not be of exactly equal duration. Methods described herein may be useful even if some time series are missing glucose readings relative to other glucose time series. Similarly, methods described herein may be useful even if some time series are lengthened or compressed relative to other time series or varying the frequency of glucose readings.

Processing may adaptively determine a first gamma parameter using glucose readings from at least two of the multiple time series and determine a barycenter using the multiple time series and the first gamma parameter. Non-limiting examples of barycenters may include a DTW barycenter or a soft DTW barycenter. Processing may subsequently apply a smoothing function to the barycenter.

Figure 2:
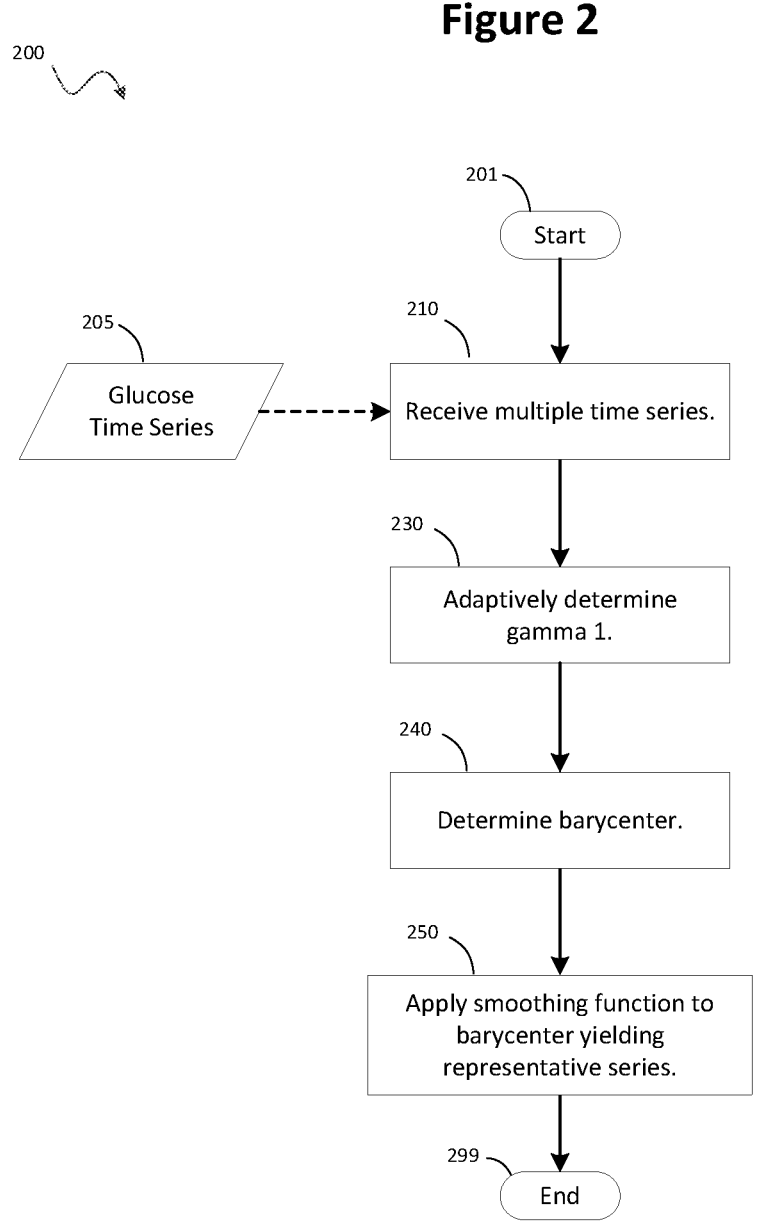
FIG. 2 presents a flowchart illustrating a method of determining a representative series using multiple glucose time series, according to certain embodiments of the present disclosure.

FIG. 2 presents a flowchart illustrating a method (200) of determining a representative series using multiple glucose time series, according to certain embodiments of the present disclosure. After the start of the method (200) at step (201), processing receives glucose time series (205) comprising multiple time series at step (210). Processing at step (230) adaptively determines a first gamma parameter using at least some of the glucose readings. Processing at step (240) subsequently determines a barycenter using the multiple time series. Finally, processing at step (250) applies a smoothing function to the bary center to yield the representative series. The method (200) ends at step (299).

In some embodiments, adaptively determining the first gamma parameter may comprise determining a series of averages in which each member of the series is an average of a set of glucose readings. As used herein, "average" may refer to any measure of central tendency including, without limitation, Euclidian mean, weighted mean, median, mode, and moving average. In some embodiments, each reading of the set may be generated at a particular quantity of time (or sequence order) relative to the start time (or first reading) of the time series during which it was generated. As a non-limiting example, if readings are generated at five minute intervals, the first average in the series may be the average of readings generated at the respective start times of their time series, the second average in the series may be the average of readings generated five minutes after the respective start times of their time series, and so on. In some embodiments, each of the averages may aggregate readings within a time range of respective start times. As a non-limiting example, if readings are generated approximately every five minutes, the first average in the series may be the average of readings generated within 2.5 minutes of (before or after) the start of the time series, the second average in the series may be the average of readings generated between 2.5 and 7.5 minutes after the respective start times, and so on. In some embodiments, each of the averages may aggregate readings by sequence position. As a non-limiting example, the first average in the series may be the average of first readings generated in the respective time series, the second average may be the average of second readings generated after the start of respective time series, and so on.

In some embodiments, adaptively determining the first gamma parameter may comprise determining a DTW distance between each of multiple glucose time series and a series of averages (such as that referenced above). As used herein, DTW may be used as an abbreviation for dynamic time warping and techniques related to dynamic time warping. Processing may subsequently determine an average of the multiple DTW distances. Some embodiments may use a function of average DTW distance to determine the first gamma parameter.

Figure 3:
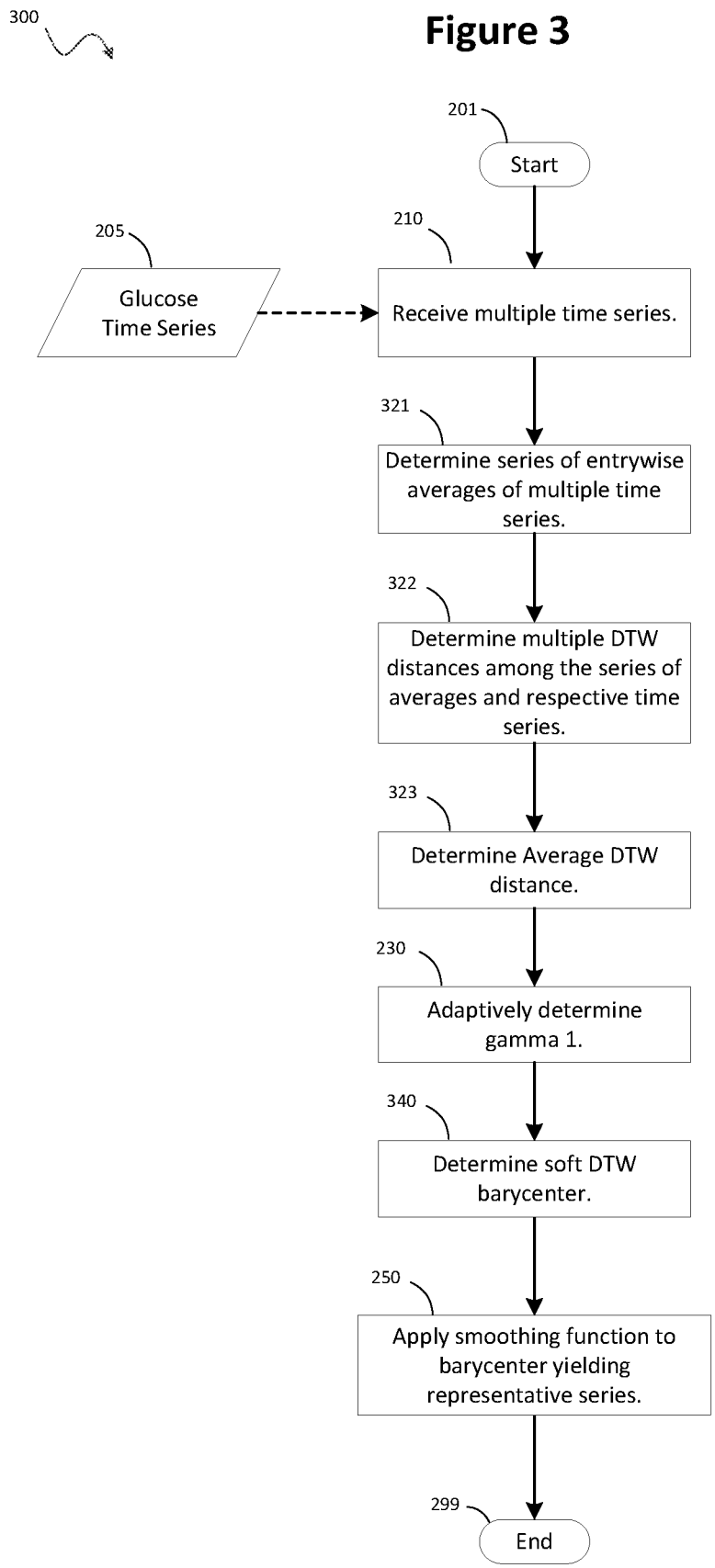
FIG. 3 presents a flowchart illustrating a method of determining a representative series comprising a soft DTW (dynamic time warping) barycenter of multiple glucose time series, according to certain embodiments of the present disclosure.

FIG. 3 presents a flowchart illustrating a method (300) of determining a representative series comprising a soft DTW barycenter of multiple glucose time series, according to certain embodiments of the present disclosure. After the start of the method (300) at step (201), processing receives glucose time series (205) that comprise multiple time series at step (210). Processing at step (321) determines a series of averages, each average of the series being an entrywise average of readings of the multiple time series. Entrywise averages may comprise, as a non-limiting example, readings generated at a common time or sequence position relative to the respective start times of the multiple time series. Processing at step (322) determines multiple DTW distances, each of the DTW distances being a DTW distance between one of the multiple time series and the series of averages. Processing at step (323) subsequently determines an average of the multiple DTW distances. Processing at step (230), like the same step of method (200), adaptively determines a first gamma parameter using the average of the multiple DTW distances. Processing at step (340) then determines a soft DTW barycenter of the multiple time series using the first gamma parameter. Finally, processing at step (250), like the same step of method (200), applies a smoothing function to the soft DTW barycenter to yield the representative series. The method (300) ends at step (299), analogous to step (299) of method (200).

In some embodiments, the first gamma parameter may be determined as a function of an average DTW distance. As a non-limiting example, in some embodiments, the average DTW distance may be compared to a threshold. If the average DTW distance exceeds the threshold, some embodiments may determine the first gamma parameter to be a multiple of the average DTW distance. If the average DTW distance does not exceed the threshold, some embodiments may determine the first gamma parameter to be a predetermined constant.

Figure 4:
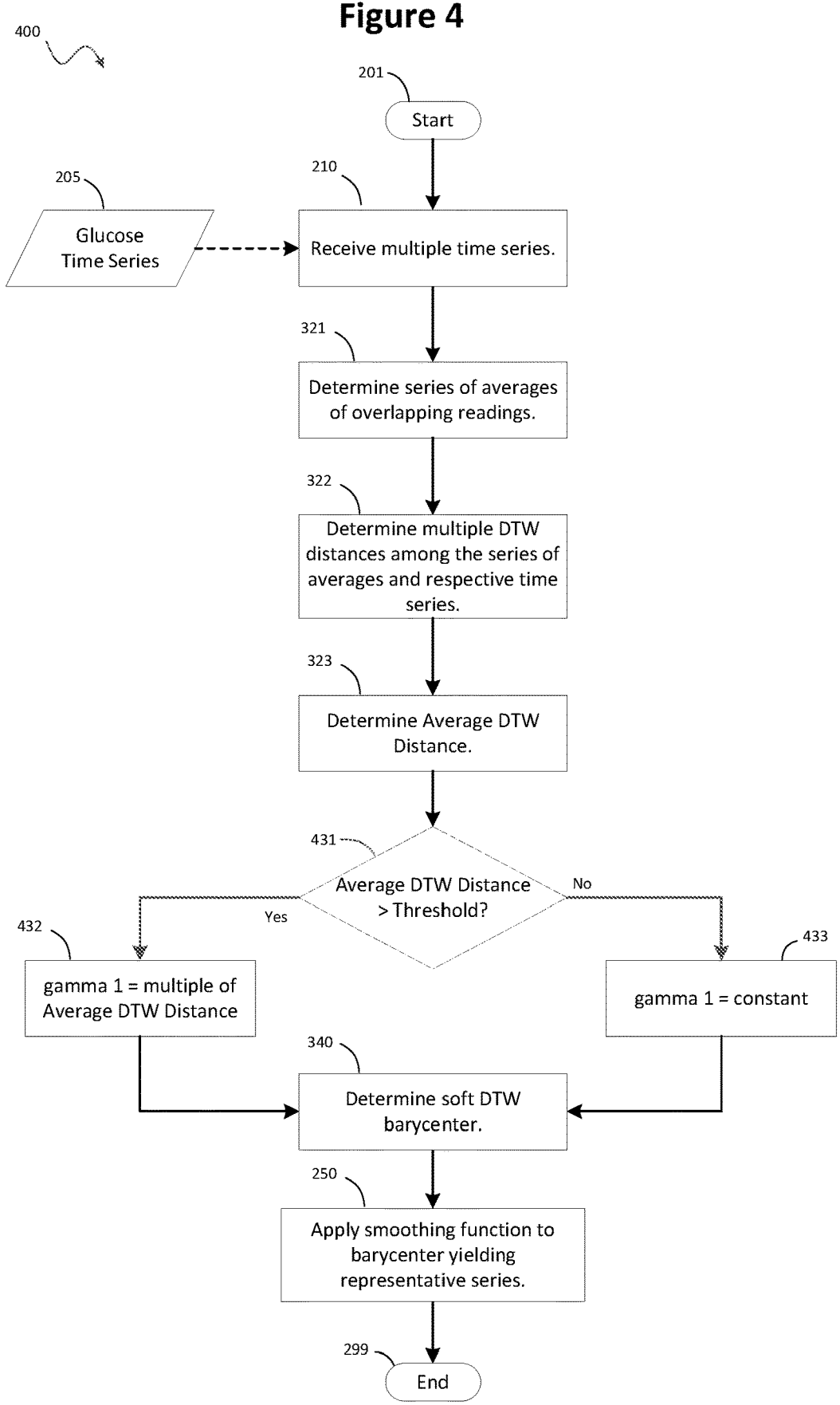
FIG. 4 presents a flowchart illustrating a method of determining a representative series in which a gamma parameter is determined using a DTW distance threshold, according to certain embodiments of the present disclosure.

FIG. 4 presents a flowchart illustrating a method (400) of determining a representative series in which a gamma parameter is determined using a DTW distance threshold, according to certain embodiments of the present disclosure. After the start of the method (400) at step (201), processing receives glucose time series (205) comprising multiple time series at step (210), analogous to step (210) of method (200). Processing at step (321) determines a series of averages, each average in the series being an entrywise average of readings of the multiple time series. Entrywise readings may comprise, as a non-limiting example, readings generated at a common time or sequence position relative to the start times of the respective time series of the multiple time series. Processing at step (322) determines multiple DTW distances, each of the DTW distances being a DTW distance between one of the multiple time series and the series of averages. Processing subsequently at step (323), like the same step in method (300) determines an average of the multiple DTW distances. Processing then at step (431) determines whether the average DTW distance exceeds a threshold. If the average DTW distance exceeds the threshold, processing in step (432) determines a first gamma parameter to be a multiple of the average DTW distance. If the average DTW distance does not exceed the threshold, processing in step (433) determines the first gamma parameter to be a predetermined constant. Processing in step (340), like the same step in method (300), determines a soft DTW barycenter using the first gamma parameter. Finally, processing in step (250), like the same step in method (200), applies a smoothing function to the soft DTW barycenter to yield the representative series of the multiple glucose time series. The method (400) ends at step (299), analogous to step (299) of method (200).

In addition to generating a representative series, some embodiments may additionally generate one or more aggregate uncertainty series. As used herein, an uncertainty series is a series of uncertainty measures. Non-limiting examples of uncertainty measures include percentiles, standard deviation, standard error, mean deviation, median deviation, or any other uncertainty measure. As used herein, aggregate uncertainty series refers to those uncertainty series determined relative to an aggregate series and may be distinguished from uncertainty series determined relative to unaltered glucose time series. An aggregate series may be a series that is generally representative of multiple time series and an aggregate series may or may not differ from the representative series discussed herein. Some aggregate series may be determined as a function of a representative series. Embodiments determining aggregate uncertainty series may determine multiple aligned series using a subset of the multiple time series, a second gamma parameter, and an aggregate series. In some embodiments, the subset of the multiple time series comprises all of the multiple time series. In some embodiments, the first gamma parameter may be equal to the second gamma parameter. Alternatively, and by way of non-limiting example, some embodiments may use a $50^{th}$ percentile of aligned series as an aggregate series. However, those familiar with the art will appreciate that the second gamma parameter may differ to some degree from the first gamma parameter without eliminating the utility of the method. Some embodiments may determine the aggregate uncertainty series using the multiple aligned series and the aggregate series.

Figure 5:
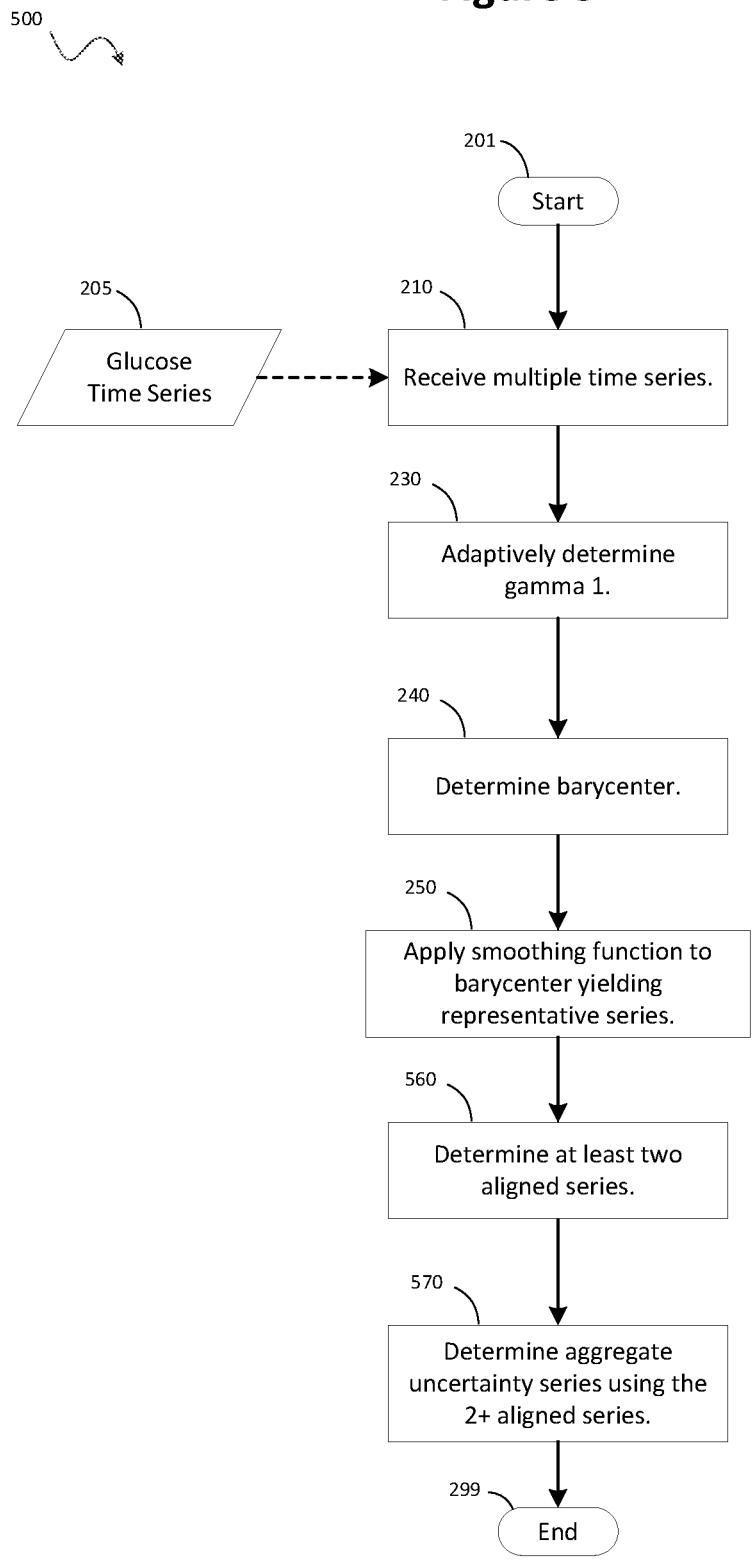
FIG. 5 presents a flowchart illustrating a method of determining one or more aggregate uncertainty series, according to certain embodiments of the present disclosure.

FIG. 5 presents a flowchart illustrating a method (500) of determining one or more aggregate uncertainty series, according to certain embodiments of the present disclosure. After the start of method (500) at step (201), processing receives glucose time series (205) that comprise multiple time series at step (210). Processing at step (230), like the same step of method (200), adaptively determines a first gamma parameter using at least some of the glucose readings from the time series. Processing subsequently at step (240), like the same step of method (200), determines a barycenter using the multiple time series and applies at step (250), like the same step of method (200), a smoothing function to the barycenter to yield a representative series. Processing next at step (560) determines at least two aligned series using a subset of the multiple time series, a second gamma parameter, and an aggregate series (which may or may not be equal to the representative series). Processing subsequently at step (570) determines at least one aggregate uncertainty series using the multiple aligned series and the aggregate series. The method (500) ends at step (299), analogous to step (299) of method (200).

Some embodiments that determine aggregate uncertainty series determine multiple aligned series using an average alignment matrix for each of the aligned series. Processing may determine each of the aligned series using one of the multiple time series, an aggregate series, an average alignment matrix, and a second gamma parameter. The average alignment matrix used with a particular time series is determined using the particular time series, the second gamma parameter, and the aggregate series. As noted, the aggregate series may or may not differ from the representative series and the second gamma parameter may or may not differ from the first gamma parameter. Processing may then determine an aligned series as a series of weighted averages in which each weighted average is determined by averaging the particular time series weighted by a column of the average alignment matrix. Each constituent of the weighted average may comprise a member of the particular glucose time series. By way of non-limiting example, the constituents of each weighted average may be consecutive readings of the glucose time series and each constituent reading may be weighted by an entry in a column of the average alignment matrix. The sum of the weighted constituents may be divided by the sum of the entries in the column of the average alignment matrix used to weight the constituents. Aggregate uncertainty series may then be determined using the multiple aligned series.

Figure 6:
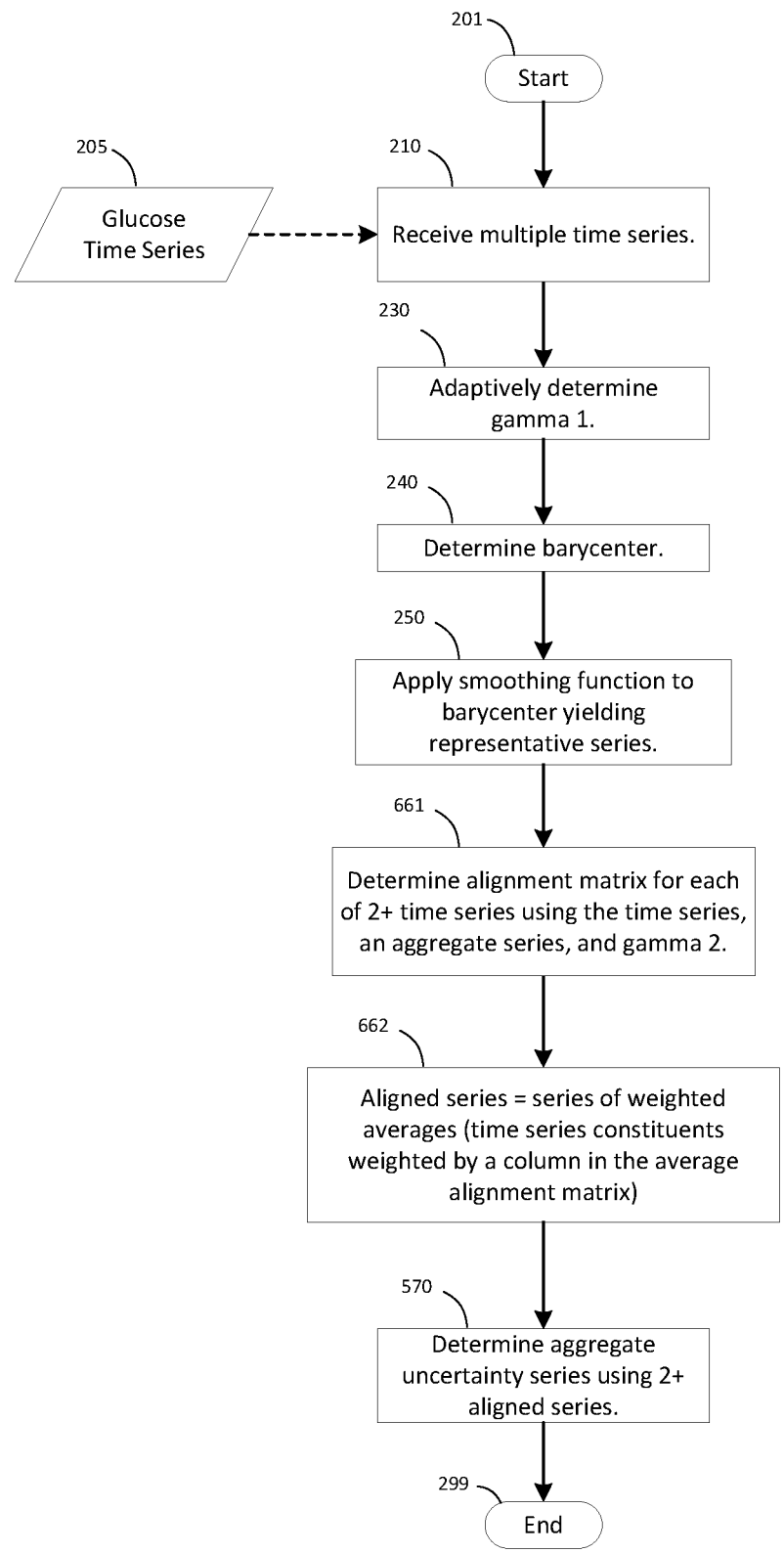
FIG. 6 presents a flowchart illustrating a method of determining one or more aggregate uncertainty series using aligned series, according to certain embodiments of the present disclosure.

FIG. 6 presents a flowchart illustrating a method (600) of determining one or more aggregate uncertainty series using an average alignment matrix and series of weighted averages, according to certain embodiments of the present disclosure. After the start of method (600) at step (201), processing receives glucose time series (205) that comprise multiple time series at step (210). Processing adaptively in step (230), like the same step in method (200) determines a first gamma parameter using at least some of the glucose readings. Processing then in step (240), like the same step in method (200), determines a barycenter using the multiple time series. Processing applies in step (250), like the same step in method (200), a smoothing function to the barycenter to yield the representative series. For each of at least two time series, processing in step (661) determines an average alignment matrix using the respective time series, an aggregate series, and a second gamma value. For each of the at least two time series, processing then in step (662) determines an aligned series as a series of weighted averages in which each constituent of each average is a member of the time series and each constituent is weighted by an entry in a column of the average alignment matrix. Processing determines in step (670) an aggregate uncertainty series using multiple aligned series. The method (600) ends at step (299), analogous to step (299) of method (200).

Some embodiments determine an uncertainty measure for at least two aligned series. Uncertainty measures of aligned curves may be determined using methods similar to those used to determine traditional uncertainty measures with the difference that the uncertainty measures are determined using aligned curves rather than series of glucose readings.

In some embodiments, the aggregate uncertainty series may be an aggregate percentile series of aligned series. As a non-limiting example, 75 percent of the aligned series would be less than an aggregate $75^{th}$ percentile series (with the remaining 25 percent of the aligned series being greater than the $75^{th}$ percentile series).

Figure 7:
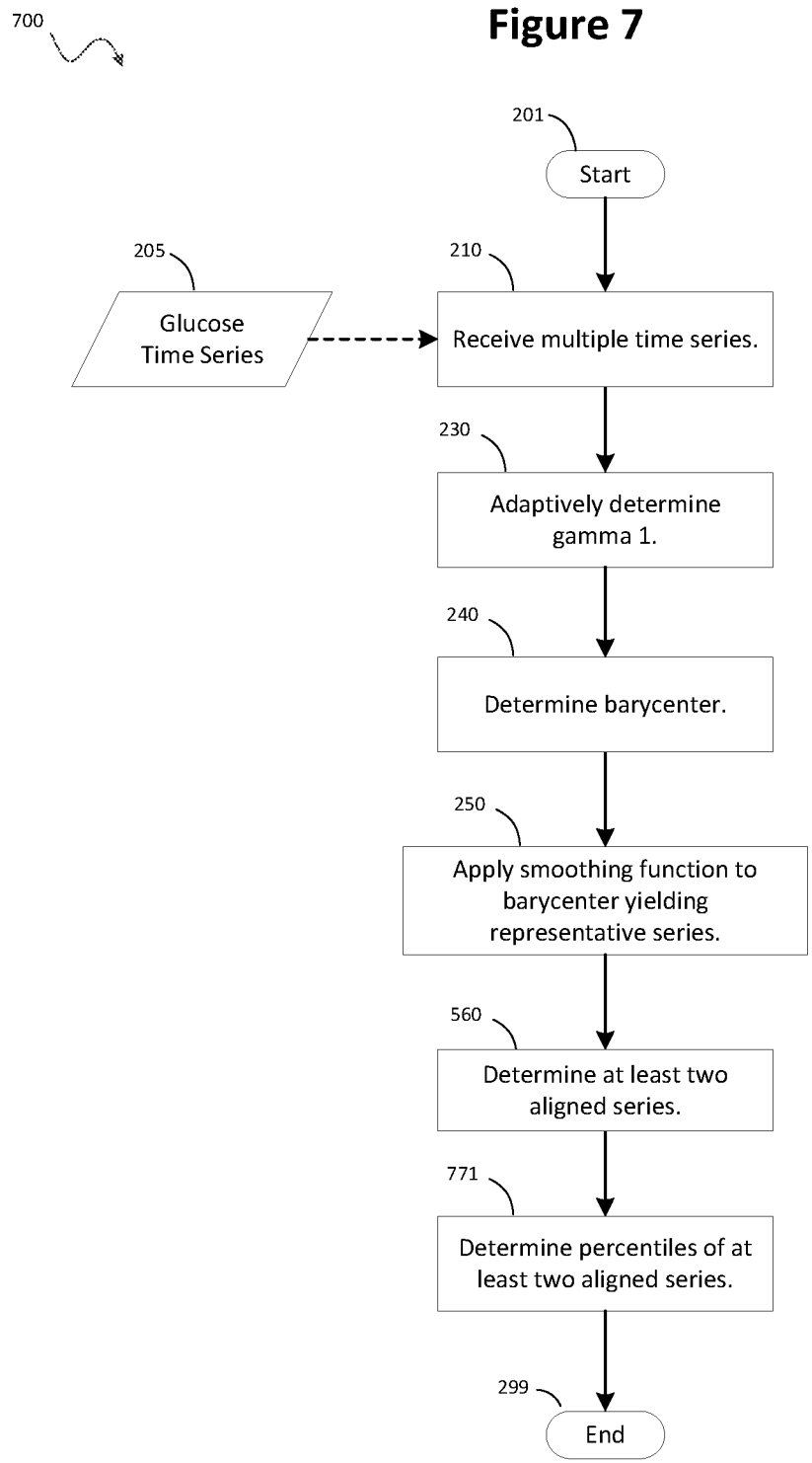
FIG. 7 presents a flowchart illustrating a method of determining one or more aggregate uncertainty series as percentiles of aligned series, according to certain embodiments of the present disclosure.

FIG. 7 presents a flowchart illustrating a method (700) of determining one or more aggregate uncertainty series as percentiles of aligned series, according to certain embodiments of the present disclosure. After the start of method (700) at step (201), processing receives glucose time series (205) that comprise multiple time series at step (210). Processing in step (230), like the same step in method (200), adaptively determines a first gamma parameter using at least some of the glucose readings. Processing subsequently in step (240), like the same step in method (200), determines a bary center using the multiple time series. Processing in step (250), like the same step in method (200), applies a smoothing function to the barycenter to yield the representative series. Processing next in step (560), like the same step in method (500), determines at least two aligned series using a subset of the multiple time series, a second gamma parameter (which may or may not be equal to the first gamma parameter), and an aggregate series (which may or may not be equal to the representative series). Processing determines in step (771) percentiles of the at least two aligned series. The method (700) ends at step (299), analogous to step (299) of method (200).

In some embodiments, processing may determine an aggregate uncertainty series by first taking a difference between two percentile series (percentiles of the aligned series) and then adding that difference to the representative series. The difference between the two percentile series is a series. As a non-limiting example, processing may take the difference between a $75^{th}$ percentile for the aligned series and a $50^{th}$ percentile for the aligned series and add that difference to the representative series to yield an aggregate $75^{th}$ percentile series.

Figure 8:
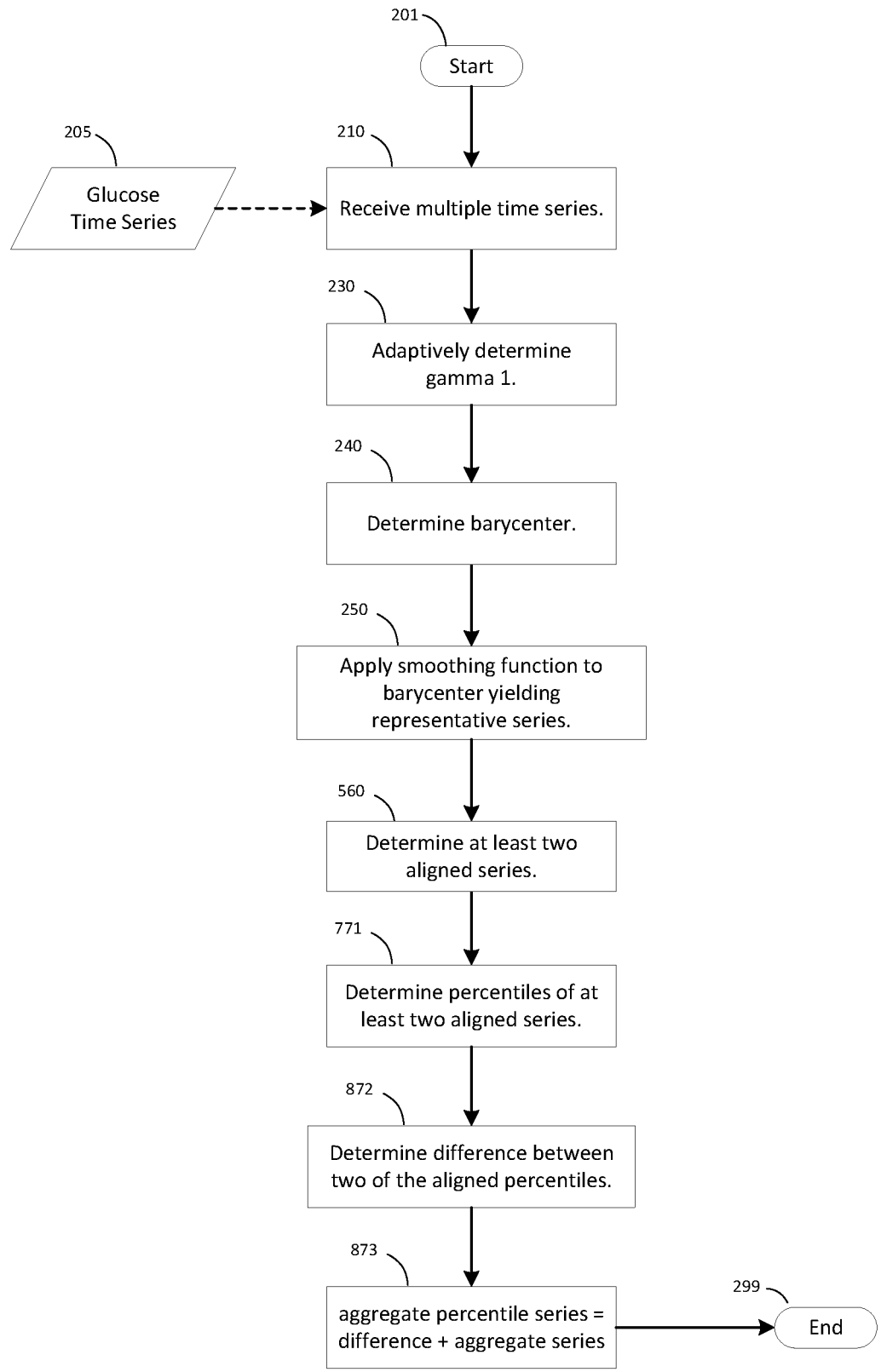
FIG. 8 presents a flowchart illustrating a method of determining one or more aggregate uncertainty series using differences between aligned percentiles, according to certain embodiments of the present disclosure.

FIG. 8 presents a flowchart illustrating a method (800) of determining one or more aggregate percentile series using differences between aligned percentiles, according to certain embodiments of the present disclosure. After the start of method (800) at step (201), processing receives glucose time series (205) that comprise multiple time series at step (210). Processing adaptively determines in step (230), like the same step in method (200), a first gamma parameter using at least some of the glucose readings. Processing subsequently in step (240), like the same step in method (200), determines a bary center using the multiple time series. Processing in step (250), like the same step in method (200), applies a smoothing function to the barycenter to yield the representative series. Processing next in step (560), like the same step in method (500), determines at least two aligned series using a subset of the multiple time series, a second gamma parameter, and an aggregate series (which may or may not be equal to the representative series). Processing determines in step (771), like the same step in method (700), percentiles of the at least two aligned series. Processing next in step (872) determines a difference between two of the aligned percentiles. Finally, processing determines in step (873) the aggregate percentile series as the difference between the aligned percentiles added to the representative series determined in step (250). The method (800) ends at step (299), analogous to step (299) of method (200).

In some embodiments, an aggregate uncertainty series may be determined using standard deviations of multiple aligned series. The standard deviations of the multiple aligned series may be expressed as an aligned standard deviation series. Some embodiments may determine an upper standard deviation series as the representative series plus the aligned standard deviation series. Some embodiments may determine a lower standard deviation series as the representative series minus the aligned standard deviation series.

Figure 9:
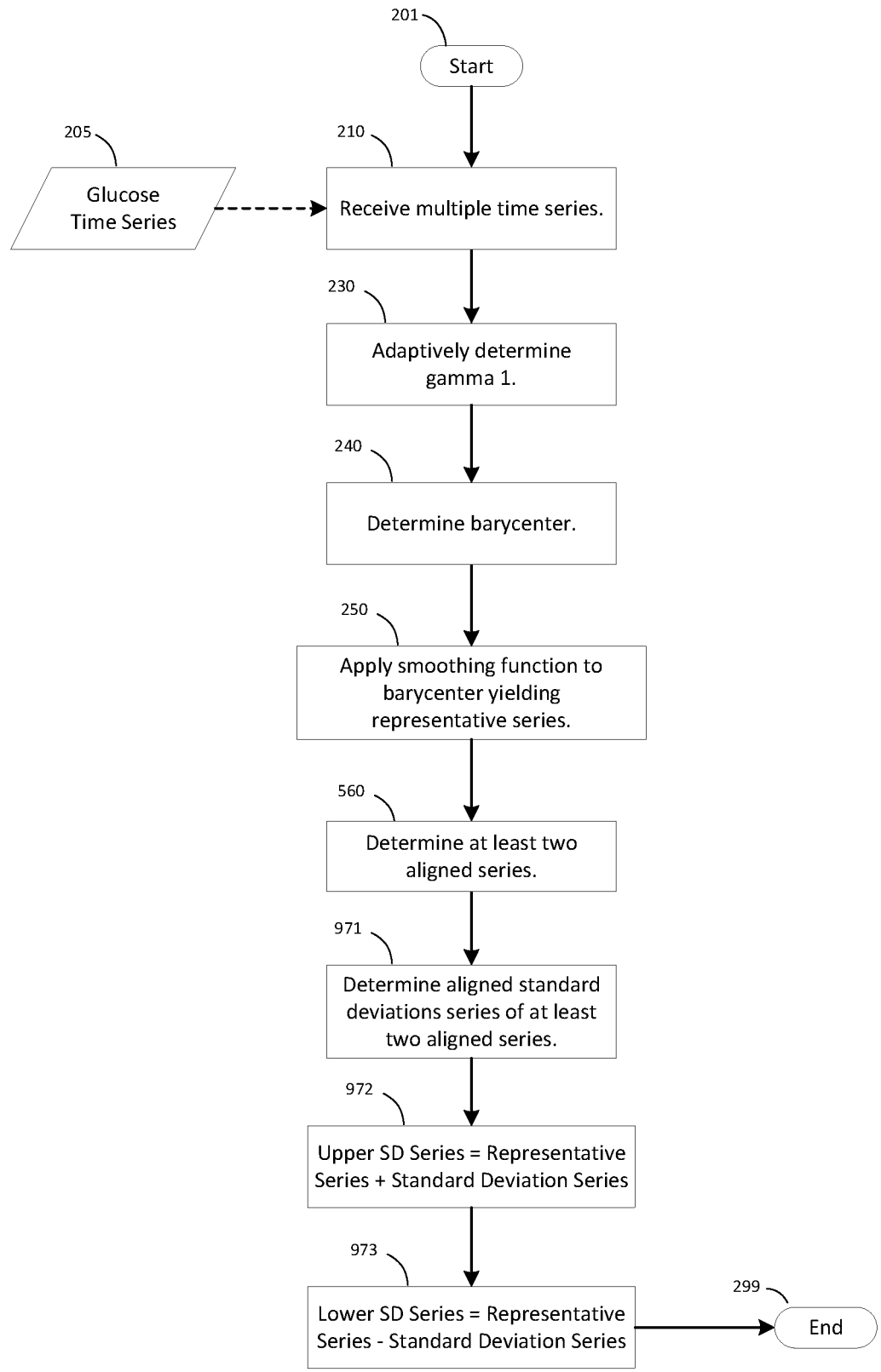
FIG. 9 presents a flowchart illustrating a method of determining one or more aggregate uncertainty series using standard deviations of aligned series, according to certain embodiments of the present disclosure.

FIG. 9 presents a flowchart illustrating a method (900) of determining one or more aggregate uncertainty series using standard deviations of aligned series, according to certain embodiments of the present disclosure. After the start of method (900) at step (201), processing receives glucose time series (205) that comprise multiple time series at step (210). Processing in step (230), like the same step in method (200), adaptively determines a first gamma parameter using at least some of the glucose readings. Processing subsequently in step (240), like the same step in method (200), determines a barycenter using the multiple time series. Processing applies in step (20), like the same step in method (200), a smoothing function to the barycenter to yield the representative series. Processing next determines in step (560), like the same step in method (500), at least two aligned series using a subset of the multiple time series, a second gamma parameter (which may or may not be equal to the first gamma parameter), and an aggregate series (which may or may not be equal to the representative series). Processing determines in step (971) an aligned standard deviation series of the at least two aligned series. Processing determines in step (972) an upper standard deviation uncertainty series as the representative series plus the aligned standard deviation series. Processing determines in step (973) a lower standard deviation uncertainty series as the representative series minus the aligned standard deviation series. The method (900) ends at step (299), analogous to step (299) of method (200).

Some embodiments display the representative series on a user interface. Non-limiting examples of user interfaces on which a representative series may be displayed include display monitors, image projectors, printers, and touch screens. Some embodiments display aggregate uncertainty series on user interfaces, either on their own or in combination with a representative series. Such embodiments may be particularly useful considering the intuitive value of the representative series and the aggregate uncertainty series.

Figure 10:
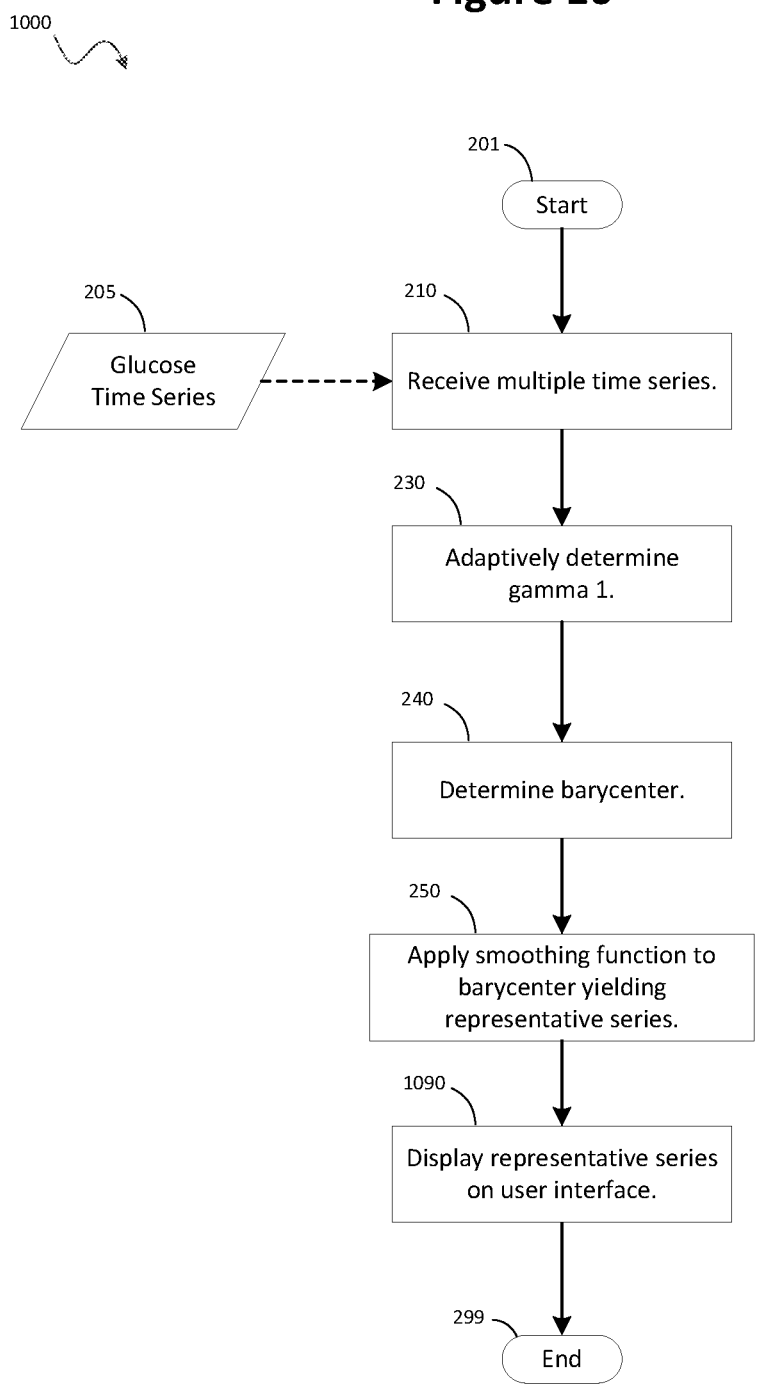
FIG. 10 presents a flowchart illustrating a method of determining a representative series and displaying the representative series on a user interface, according to certain embodiments of the present disclosure.

FIG. 10 presents a flowchart illustrating a method (1000) of determining a representative series of multiple glucose time series in which the representative series is displayed on a user interface, according to certain embodiments of the present disclosure. After the start of method (1000) at step (201), processing receives glucose time series (205) that comprise multiple time series at step (210). Processing adaptively determines in step (230), like the same step in method (200), a first gamma parameter using at least some of the glucose readings. Processing subsequently determines in step (240), like the same step in method (200), a barycenter using the multiple time series. Processing applies in step (250), like the same step in method (200), a smoothing function to the barycenter to yield the representative series. Processing sends information in step (1090) to a user interface causing the user interface to display the representative series. The method (1000) ends at step (299), analogous to step (299) of method (200).

Figure 11:
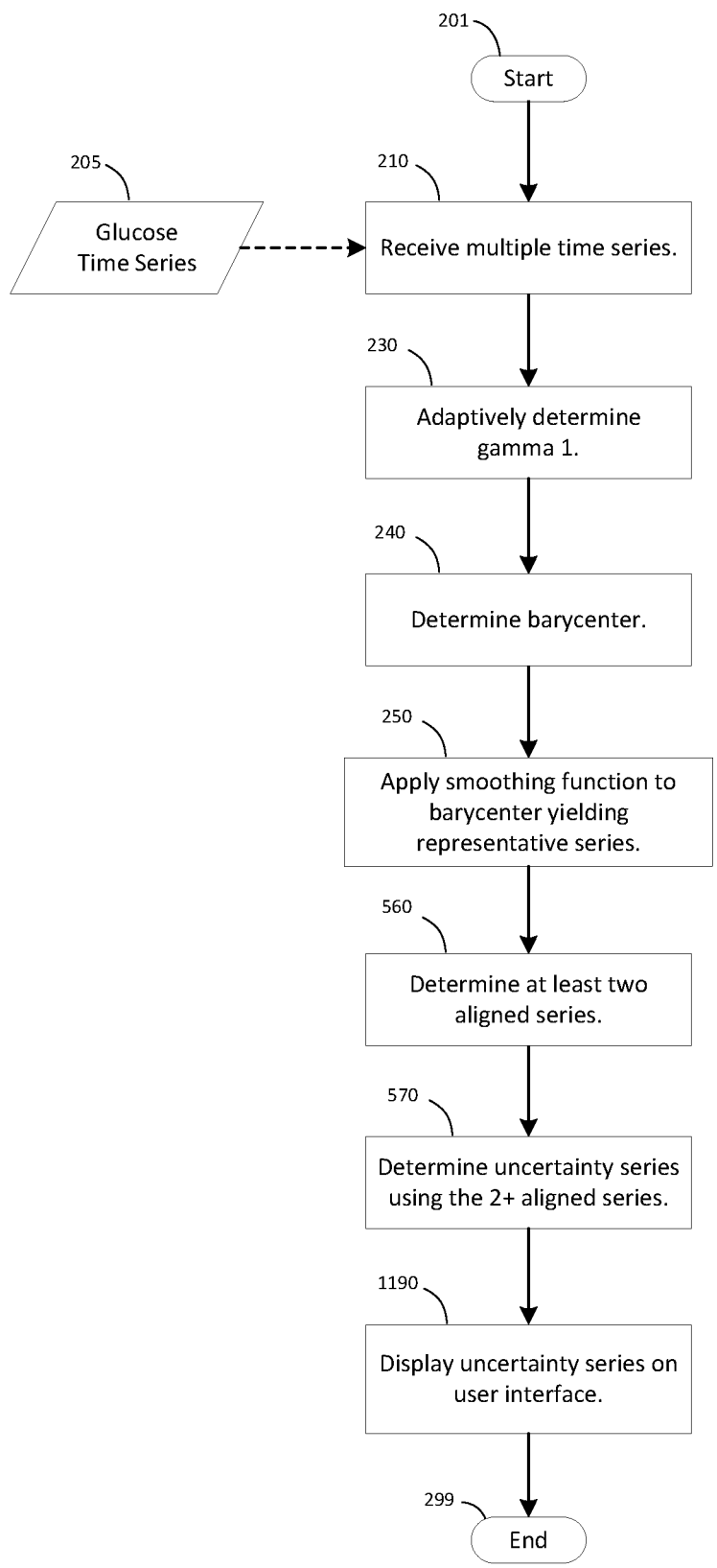
FIG. 11 presents a flowchart illustrating a method of determining one or more aggregate uncertainty series and displaying the aggregate uncertainty series on a user interface, according to certain embodiments of the present disclosure.

FIG. 11 presents a flowchart illustrating a method (1100) of determining one or more aggregate uncertainty series and displaying the uncertainty series on a user interface, according to certain embodiments of the present disclosure. After the start of method (1100) at step (201), processing receives glucose time series (205) that comprise multiple time series at step (210). Processing adaptively determines in step (230), like the same step in method (200), a first gamma parameter using at least some of the glucose readings. Processing subsequently determines in step (240), like the same step in method (200), a barycenter using the multiple time series. Processing applies in step (250), like the same step in method (200), a smoothing function to the barycenter to yield the representative series. Processing next determines in step (560), like the same step in method (500), at least two aligned series using a subset of the multiple time series, a second gamma parameter, and an aggregate series. Processing subsequently determines in step (570), like the same step in method (500), at least one aggregate uncertainty series using the multiple aligned series and the aggregate series. Processing sends information in step (1190) to a user interface causing the user interface to display the aggregate uncertainty series. The method (1100) ends at step (299), analogous to step (299) of method (200).

Figure 1:
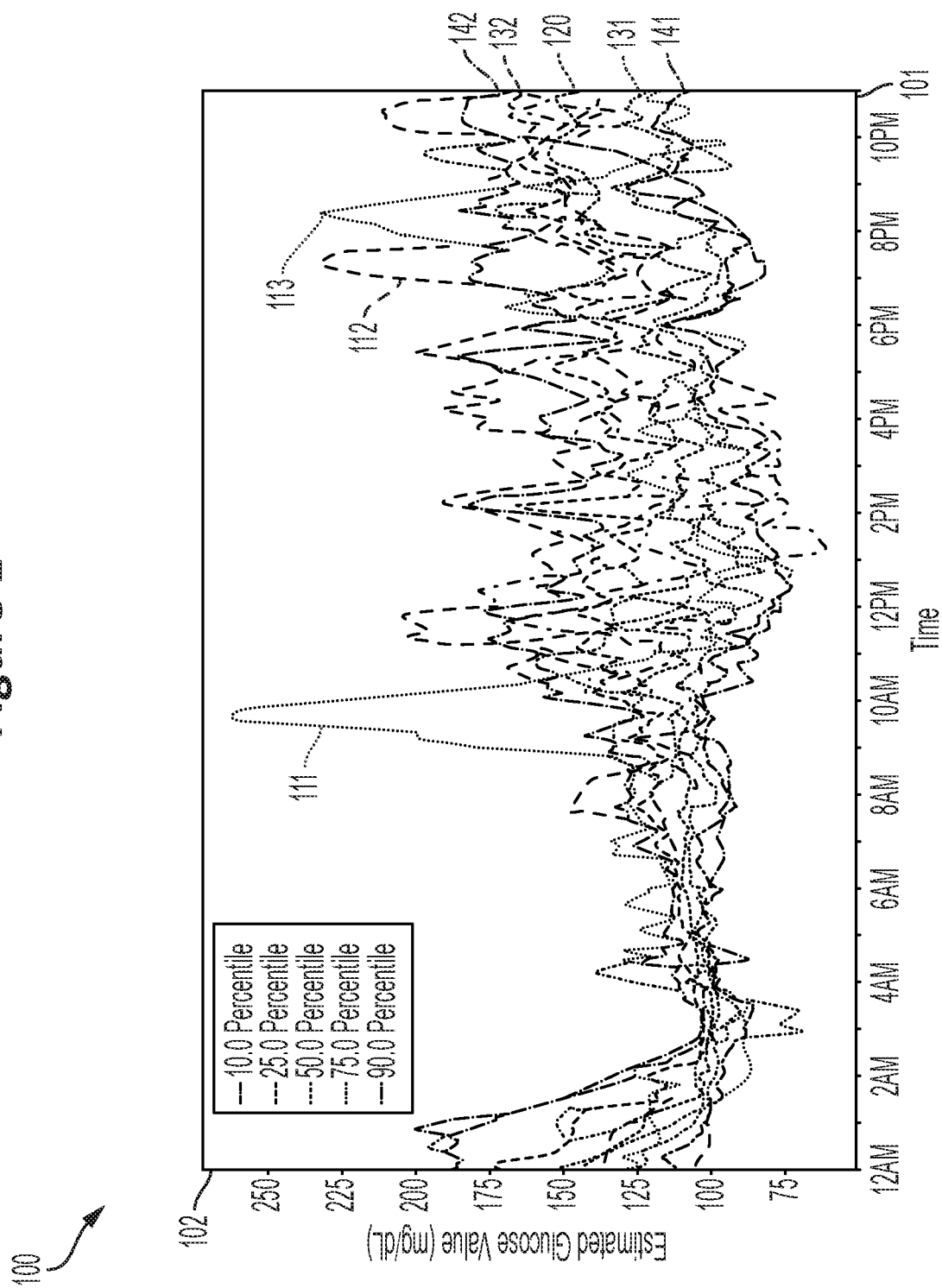
FIG. 1 presents a graph of multiple 24-hour glucose time series superimposed in an entrywise fashion with multiple percentile series.
Figure 12:
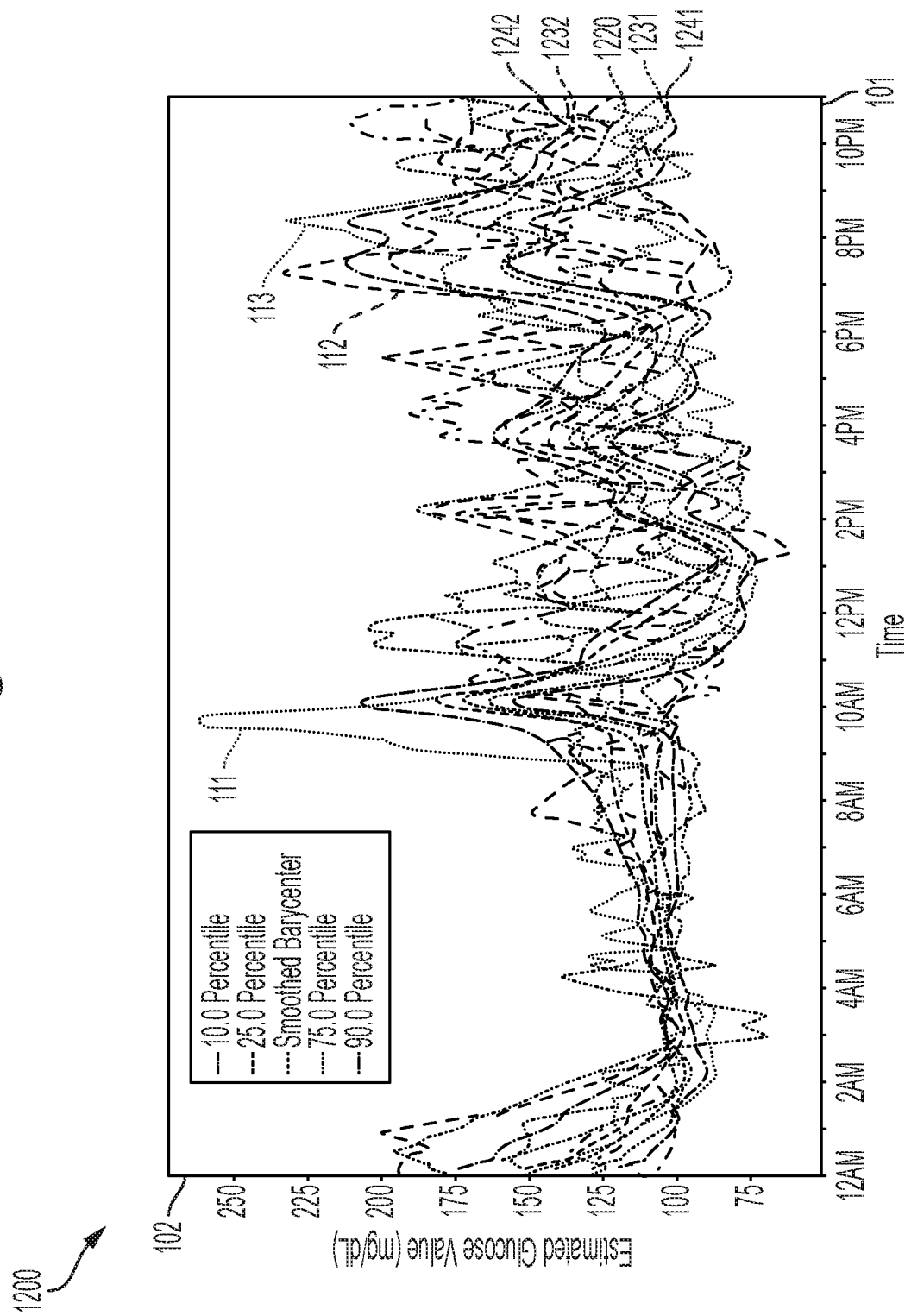
FIG. 12 presents a graph comprising a smoothed barycenter of multiple 24-hour glucose time series and multiple aggregate percentile series, according to certain embodiments of the present disclosure.

FIG. 12 presents a graph (1200) comprising a smoothed bary center of multiple 24-hour glucose time series and multiple aggregate percentile series, according to certain embodiments of the present disclosure. The horizontal (x) axis (101) represents time of day over a 24-hour period. The vertical (v) axis (102) represents estimated glucose value (EGV) as glucose concentration in milligrams per deciliter. The pale, dashed curves (e.g. 111, 112, 113) on the plot are glucose time series for respective days. (The glucose time series in FIG. 12 are identical to the glucose time series in FIG. 1.) A point on the graph represents EGV at a particular time of day. The red curve is a smoothed barycenter (1220) of the glucose time series-a representative series representing an aggregate of each of the individual glucose time series. The two blue curves represent aggregate $25^{th}$ and $75^{th}$ percentile curves (1231, 1232), respectively, of aligned series. The two green curves represent the aggregate $10^{th}$ and $90^{th}$ percentile curves (1241, 1242), respectively, of aligned series. Each of the aggregate percentile curves is calculated with respect to aligned series that are determined using the glucose time series. The advantages of processing glucose time series using a smoothed barycenter become apparent when compared to methods of entrywise metrics such as those presented in FIG. 1. The smoothed barycenter (1220) is an output that appears to align peaks, valleys, and other features of the individual glucose series. Thus, daily patterns in glucose levels obscured by timing variations in glucose-altering behaviors (as shown in median curve 120 of FIG. 1) become apparent when using a smoothed barycenter (1220) as a representative series. Similarly, the aggregate percentile curves (1231, 1232, 1241, 1242) better represent variation of glucose readings observed in multiple glucose time series than the raw percentile series (131, 132, 141, 142) presented in FIG. 1.

Some embodiments use a representative series, an aggregate uncertainty series, or both to generate a recommendation of a behavior that, if followed, could influence glucose levels. Recommendations could suggest that the individual from whom the glucose readings were measured engage in, refrain from, or modify the amount of a behavior potentially influencing the individual's glucose levels. Some embodiments may make a recommendation based upon one or more processors identifying a particular feature in a representative series, an aggregate uncertainty series, or both. Recommendations may comprise a recommended time for a particular behavioral change, the time occurring within a threshold amount of time of the identified feature. Non-limiting examples of behaviors that may be initiated, increased, or decreased may comprise consumption of foods or particular nutrient types such as carbohydrates, physical activity (potentially including types, amounts, or intensities of physical activity), consumption (e.g. ingestion or injection) of medications or other substances influencing glucose level, meditation or mental practices potentially influencing psychological stress levels, and sleep. The one or more processors may present the recommendation on a user interface. In addition to visual user interfaces, such as those mentioned herein, user interfaces may also include audio interfaces such as a speaker or tactile interfaces such as, by way of a non-limiting example, refreshable braille displays.

Figure 13:
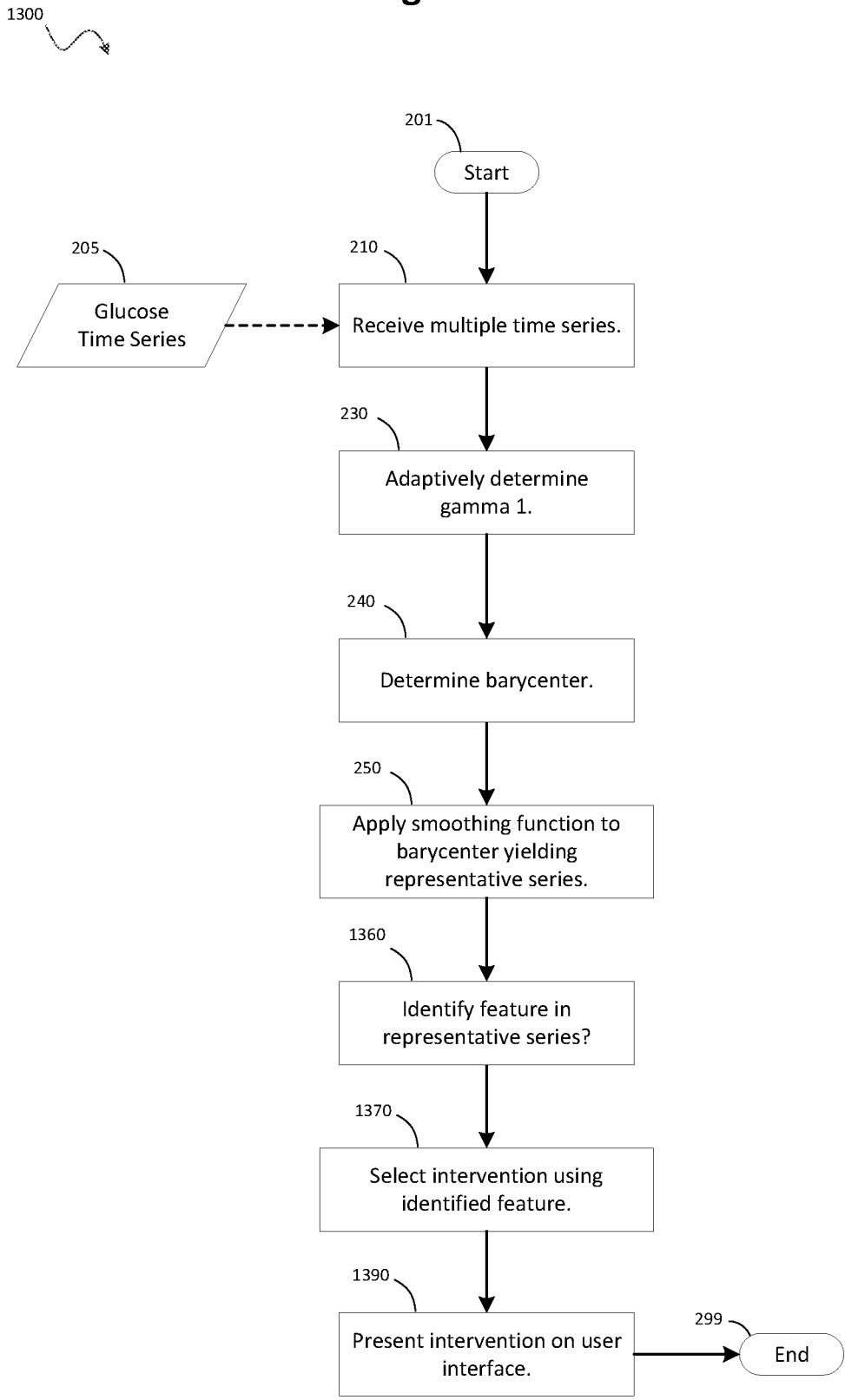
FIG. 13 presents a flowchart illustrating a method of presenting a behavioral recommendation on a user interface based on a representative series, according to certain embodiments of the present disclosure.

FIG. 13 presents a flowchart illustrating a method (1300) of presenting a behavioral recommendation on a user interface using a representative series, according to certain embodiments of the present disclosure. After the start of method (1300) at step (201), processing receives glucose time series (205) that comprise multiple time series at step (210). Processing adaptively determines in step (230), like the same step in method (200), a first gamma parameter using at least some of the glucose readings. Processing subsequently determines in step (240), like the same step in method (200), a bary center using the multiple time series. Processing applies in step (250), like the same step in method (200), a smoothing function to the barycenter to yield the representative series. Processing subsequently identifies in step (1360) a feature in the representative series. Processing then selects in step (1370) an intervention based on the identified feature. Processing presents in step (1390) the recommendation on a user interface. The method (1300) ends at step (299), analogous to step (299) of method (200).

Figure 14:
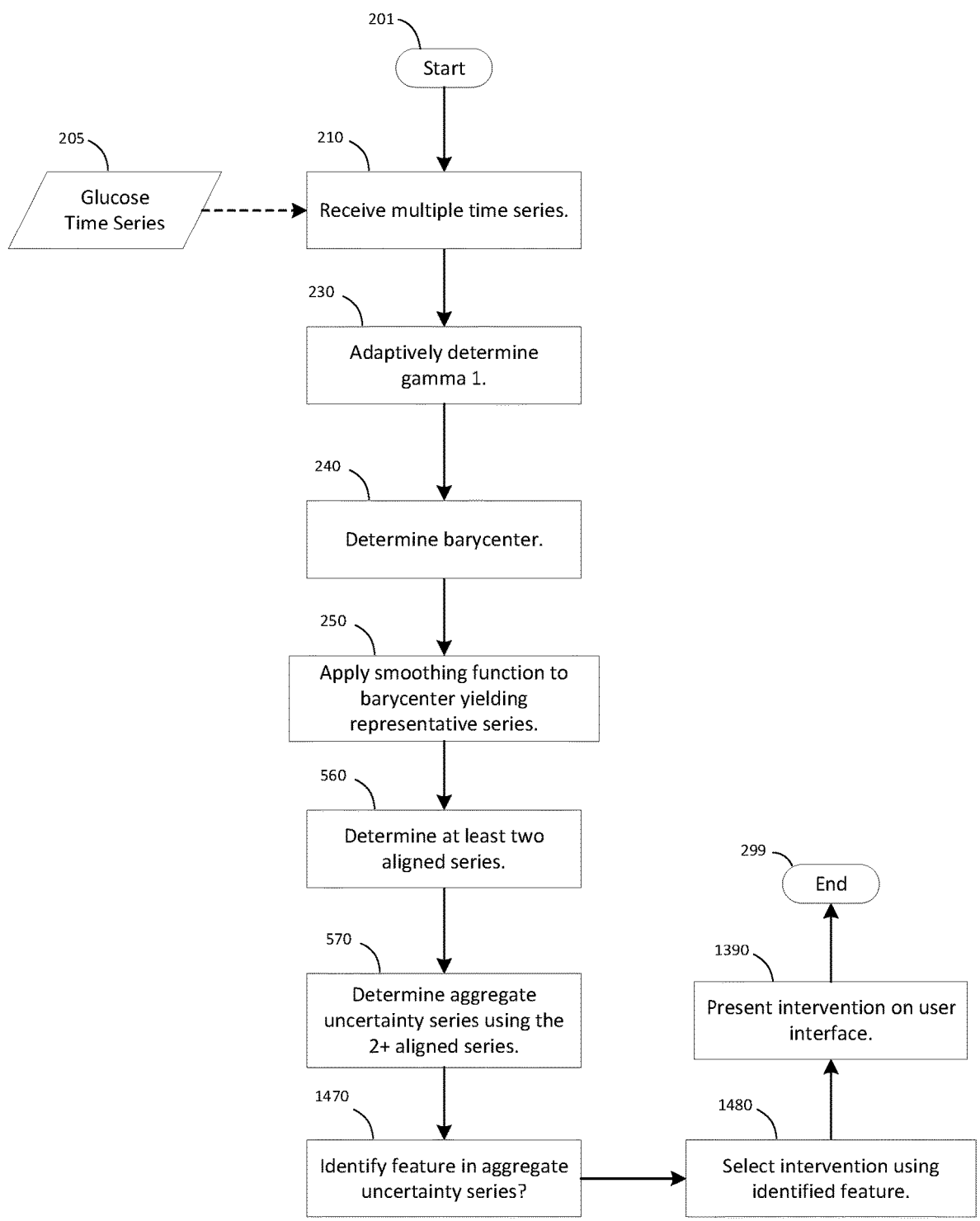
FIG. 14 presents a flowchart illustrating a method of presenting a behavioral recommendation on a user interface based on an uncertainty series, according to certain embodiments of the present disclosure.

FIG. 14 presents a flowchart illustrating a method (1400) of presenting a behavioral recommendation on a user interface based on an uncertainty series, according to certain embodiments of the present disclosure. After the start of method (1400) at step (201), processing receives glucose time series (205) that comprise multiple time series at step (210). Processing adaptively determines in step (230), like the same step in method (200), a first gamma parameter using at least some of the glucose readings from the time series. Processing subsequently determines in step (240), like the same step in method (200), a barycenter using the multiple time series and applies in step (250), like the same step in method (200), a smoothing function to the barycenter to yield a representative series. Processing next determines in step (560), like the same step in method (500), at least two aligned series using a subset of the multiple time series, a second gamma parameter, and an aggregate series (which may or may not be equal to the representative series). Processing subsequently determines in step (570), like the same step in method (500), at least one aggregate uncertainty series using the multiple aligned series and the aggregate series. Processing identifies in step (1470) a feature in the aggregate uncertainty series. Processing then selects in step (1480) an intervention based on the identified feature. Processing presents in step (1390), as in the same step in method (1300) the recommendation on a user interface. The method (1400) ends at step (299), analogous to step (299) of method (200).

System Embodiments

Embodiments include systems that determine representative series using multiple glucose time series. System embodiments may be housed in a single device or be distributed among multiple devices communicatively coupled to one another. Systems may comprise one or more processors. The term "processor" includes units comprising one or more processors and the methods described herein may be performed on one or multiple processors. The one or more processors may be communicatively coupled to and execute instructions stored on at least one computer readable data storages (CRDS) (also referred to herein as non-transitory computer-readable medium or, simply, a computer readable medium). As used herein, the term CRDS may include one CRDS or multiple CRDSs. The instructions may cause the one or more processors to determine a subset of readings to store on the CDRS. Embodiments of the CRDS may include random access memory (RAM) and various types of non-volatile memory including, but not limited to, read-only memory (ROM), programmable read-only memory (PROM), erasable programmable read-only memory (EPROM), and/or electrically erasable programmable read-only memory (EEPROM). Embodiments of the CRDS may include magnetic storage (such as hard drives, floppy disks, and magnetic tape) and/or optical storage (such as CDs and DVDs).

While the one or more processors may determine a representative series using glucose readings generated by glucose sensors, system embodiments need not comprise the glucose sensors themselves. As a non-limiting example, the glucose readings may be stored on the CRDS and processed at some time after the glucose readings were generated by the glucose sensor. Glucose sensors generating glucose readings may include, by way of non-limiting example, those in direct contact with interstitial fluids, blood, other bodily fluids, or tissues or those measuring blood glucose without direct contact including those using transmission and reflection spectroscopy. The measurement of blood glucose may be expressed as an output. The output may be analog (such as a voltage or resistance) or digital and may or may not need conversion into a value corresponding to glucose level. Outputs from a glucose sensor may be referred to herein as glucose readings or simply readings. In some embodiments, glucose sensors may provide frequent or nearly continuous measurement of glucose levels. The glucose sensor may be communicatively coupled, directly or indirectly, to one or more processors configured to determine a representative series.

System components mentioned herein may consume energy from a power source. Power sources may include various types of batteries such as, by way of non-limiting example, lithium-ion batteries, nickel metal-hydride batteries, alkaline batteries, nickel-cadmium batteries, and lead-acid batteries. Alternatively, or in addition, power sources may include devices that collect ambient energy such as electromagnetic waves, heat, motion, and force. Examples of devices capturing ambient electromagnetic energy include photovoltaic cells and antennae that generate current from electromagnetic frequencies. A variety of materials generate electrical current when exposed to a heat differential. Motion may generate electrical current using means or devices including traditional generators and piezo-electric materials, the latter of which may also generate current in response to force. Alternatively, or in addition, power sources may include electrical current provided by generators such as electricity provided through the power grids of many cities.

Figure 15:
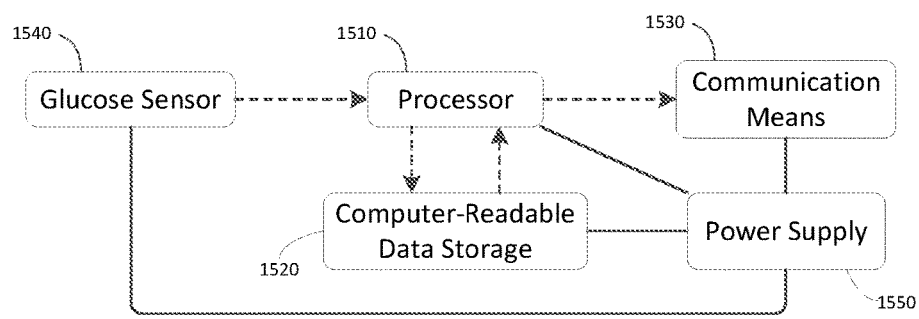
FIG. 15 illustrates a schematic diagram of a system determining a representative series from glucose readings according to certain embodiments disclosed herein.

FIG. 15 illustrates a schematic diagram of a system (1500) determining a representative series from glucose readings according to certain embodiments disclosed herein. The system (1500) comprises a processor (1510) communicatively coupled to a computer-readable data storage (CRDS) (1520). The dashed line connecting the two components indicates that they are communicatively coupled: information may be transferred from one to another but does not necessarily require a physical connection. The processor (1510) may execute instructions stored on the CRDS (1520). The processor (1510) may store and retrieve data, such as recorded glucose readings, from the CRDS (1520) and process the data to determine a representative series. The processor (1510) and CRDS (1520) are the elements of the most basic version of the system (1500). In addition, the processor (1510) may, optionally, send the one or more measures of interest to a communication module or means (1530). The communications module or means (1530)) may comprise, by way of non-limiting example, a module or means to communicate information to another component of the system or to another device (such as, for example, a wire or wireless communication means or device) or a user interface such as a display screen. In some embodiments, the user interface may be interactive. The system (1500) may, optionally, comprise a glucose sensor (1540) that is communicatively coupled to the processor (1510). The components of the system (1500) may be powered by a power supply (1550). While this diagram shows one power supply providing energy to each of the components, the system (1500) may use multiple power sources. Any configuration of power sources may be used provided that each component receives power, either directly from a power supply or indirectly through other components.

Figure 16:
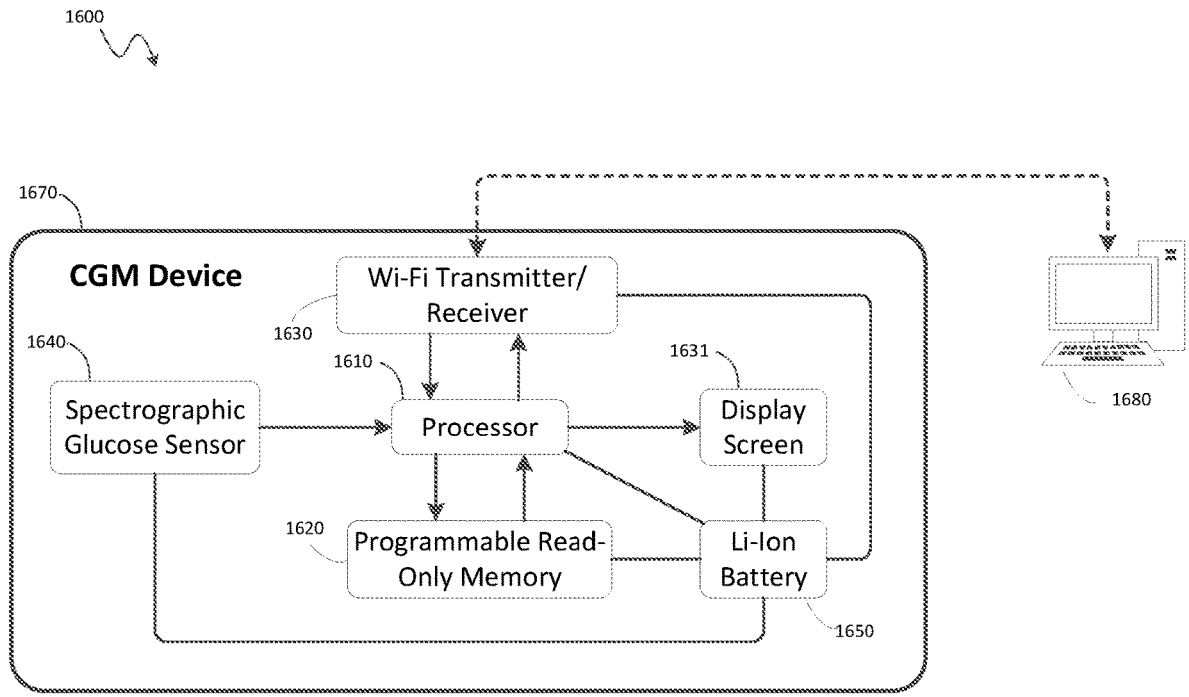
FIG. 16 illustrates a schematic diagram of a system housed in a single device determining a representative series from glucose readings, according to certain embodiments disclosed herein.

FIG. 16 illustrates a schematic diagram of a system (1600) housed in a single device (1670) determining a representative series from glucose readings, according to certain embodiments disclosed herein. The rectangle surrounding the components indicates that they are contained within a single housing of the single device (1670). The CGM device (1670) comprises a processor (1610) configured for CGM function, programmable read-only memory (PROM) (1620), a Wi-Fi transmitter-receiver (1630), a display screen (1631) visible from the outside of the device, a spectrographic glucose sensor (1640), and a rechargeable lithium-ion (Li-Ion) battery (1650). The processor (1610) executes instructions stored on the PROM (1620) for determining a representative series using glucose readings from the spectrographic glucose sensor (1640). The display screen (1631) may perform functions such as informing the user of current blood glucose levels, or visual representations of the representative series. From time to time, the single device (1670) may communicate with a second device (1680) using the Wi-Fi transmitter-receiver (1630) that exchanges information with the second device (1680), which may be an external device relative to the single housing of the single device. The wireless communication may serve to communicate unprocessed or derived measures of blood glucose concentration to the second device (1680) which may be communicatively coupled to networks such as the Internet. The wireless communication may also be used to transfer updated instructions to the single device (1670) from the second device (1680).

Some system embodiments may comprise a user interface. In some embodiments, the interface may communicate information only from the one or more processors to the user. Such an interface could include, by way of non-limiting example, one or more of: a display screen, an audio speaker, or a tactile output. Tactile outputs may include, by way of non-limiting example, a vibration generator or refreshable braille terminal. In some embodiments, the user interface may allow the user to input information into the system. As a non-limiting example, in some embodiments, the system may include a keyboard, microphone, or touch screen allowing the user to enter information related to glucose levels such as the type, time, and amount of food consumed: the amount, type, time, frequency, and intensity of physical activity: medications taken, at what time, and in what amount: emotional state, energy level, location, or an environmental condition.

Figure 17:
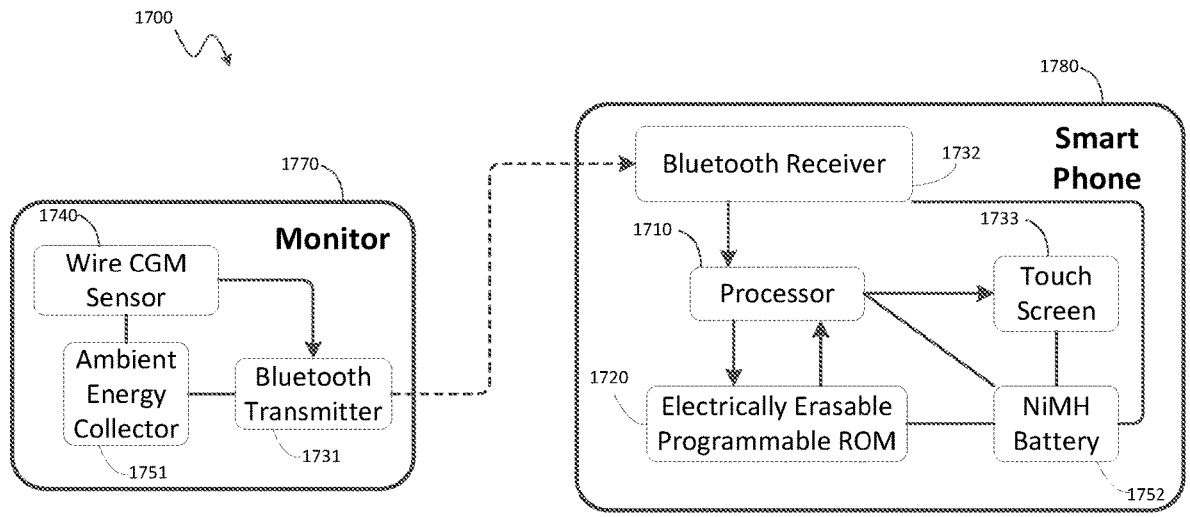
FIG. 17 illustrates a schematic diagram of a system determining a representative series in which a glucose sensor housed in a first device transmits data wirelessly to a processor housed in a second device, according to certain embodiments disclosed herein.

FIG. 17 illustrates a schematic diagram of a system (1700) determining a representative series in which a wire-based glucose sensor (1740) housed in a first device (1770) transmits data wirelessly to a processor (1710) housed in a second device (1780)), according to certain embodiments disclosed herein. In this embodiment, the second device (1780) is a smartphone. The first device (1770), which may be a glucose monitor, contains a wire-based glucose sensor (1740) that may be inserted through the skin of the user, a Bluetooth transmitter (1731), and an ambient energy collector (1751) to power the other components. The ambient energy collector (1751) may capture energy from, for example, the user's body heat, body motion, or from ambient light or other electromagnetic waves. The Bluetooth transmitter (1731) may transmit raw (unprocessed) glucose data to a Bluetooth receiver (1732) in the second device (1780). The Bluetooth receiver (1732) may then relay the raw glucose data to the processor (1710) which, in turn, processes the glucose data according to instructions stored on an electrically erasable programmable read-only memory (EEPROM) (1720) and uses the glucose data to generate a representative series. The processor (1710) may then display the representative series on a touch screen (1733) on the second device (1780). Components in the second device (1780) are powered by a nickel metal-hydride (NiMH) battery (1752). The smartphone or second device (1780) could, optionally, communicate raw or processed glucose data to other external devices via cellular frequencies and data protocols. The second device (1780) could also, optionally, be used as an input device into which a user could enter data regarding subjects such as food and medication consumption and physical activity through the touch screen (1733).

Time measuring means or module(s) may be used to associate glucose readings with timestamps indicating, by way of non-limiting example, respective times at which they were generated. Time may be measured using a variety of means and devices. Because processors typically perform calculations on a regular time cycle, some embodiments may count processor cycles as a mechanism or means for measuring time. If the accelerometer generates outputs at regular time intervals, some embodiments may count the number of accelerometer outputs to measure the passage of time. Alternatively, a separate time-measuring device may be used to measure time periods. Non-limiting examples of alternative time measuring devices or means include electric clocks such as quartz clocks, motor-driven clocks, synchronous clocks, and radio-controlled clocks that are wirelessly synchronized with a time standard such as an atomic clock, or the atomic clock itself.

Figure 18:
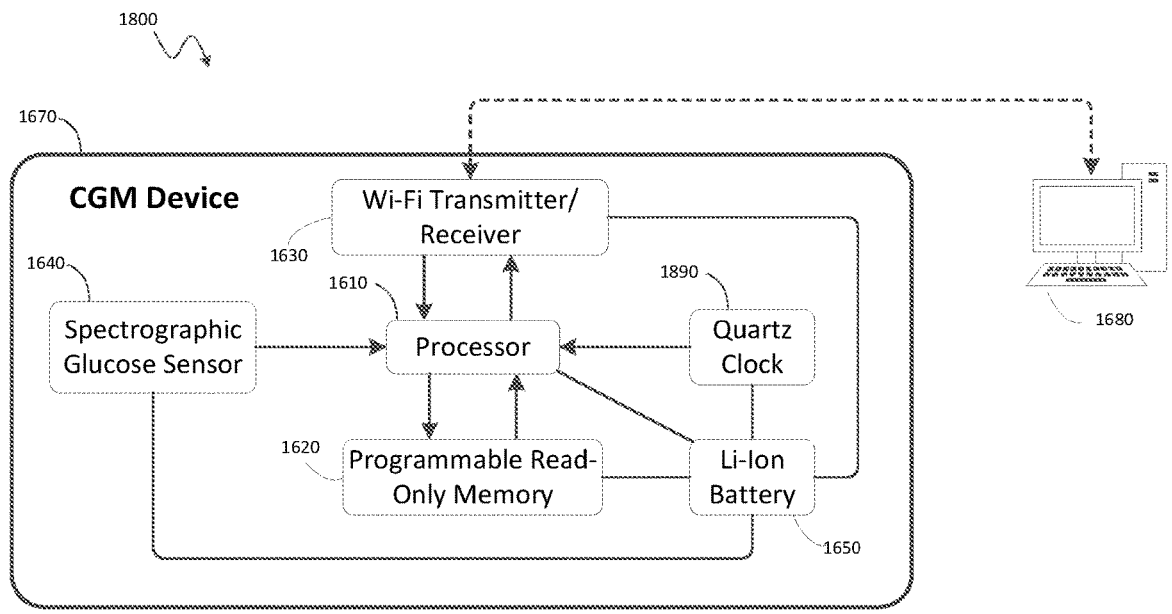
FIG. 18 illustrates a schematic diagram of a system determining a representative series in which the system comprises a quartz clock according to certain embodiments of the present disclosure.

FIG. 18 illustrates a schematic diagram of a system (1800) determining a representative series in which the system comprises a quartz clock (1890) according to certain embodiments of the present disclosure. System 1800 is substantially similar to system 1600 with the addition of a quartz clock (1890) in place of the display screen (1631). The processor (1610) is communicatively coupled to the quartz clock (1890) and uses outputs from the quartz clock (1890) to determine a representative series. The quartz clock (1890) may be used to determine, by way of non-limiting example, relative times at which glucose readings are generated.

Computer-Readable Media

Some embodiments may comprise a computer-readable data storage (CRDS) storing instructions that, when executed by one or more processors, cause the one or more processors to perform methods described herein. In particular, the instructions may direct the one or more processors to determine a representative series. Embodiments of the CRDS may include random access memory (RAM) and various types of non-volatile memory including, but not limited to, read-only memory (ROM), programmable read-only memory (PROM), erasable programmable read-only memory (EPROM), and/or electrically erasable programmable read-only memory (EEPROM). Embodiments of the CRDS may include magnetic storage (such as hard drives, floppy disks, and magnetic tape) and/or optical storage (such as CDs and DVDs). In some embodiments, the instructions may additionally direct the one or more processors to determine an uncertainty series using the representative series.

CONCLUSION

The above description is neither exclusive nor exhaustive and is intended neither to describe all possible embodiments (also called "non-limiting examples") nor to limit the scope of the embodiments. Embodiments may include elements in addition to those in the described embodiments and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless specified otherwise. Terms such as "first," "second," "third" and so forth are used as labels to distinguish elements and do not indicate sequential order unless specified otherwise. In addition to the embodiments described above, embodiments may include any that would fall within the scope of the claims, below.

What is claimed is:

1. A computer-implemented method comprising:
receiving, by one or more processors, a plurality of time series comprising a plurality of glucose readings respectively associated with a plurality of timestamps, the plurality of time series being generated during one or more time periods;
adaptively determining, by the one or more processors, a gamma parameter based at least in part on (i) the plurality of glucose readings and (ii) the plurality of timestamps respectively associated with the plurality of glucose readings;
determining, by the one or more processors, a barycenter based at least in part on the plurality of time series and the gamma parameter;
determining, by the one or more processors, a representative series of the plurality of time series associated with the plurality of glucose readings by applying a smoothing function to the barycenter; and
displaying, by the one or more processors, a graphical display of the representative series via a user interface.

2. The computer-implemented method of claim 1, wherein adaptively determining the gamma parameter comprises:
determining a series of averages, wherein determining a first average of the series of averages comprises determining an average glucose reading using a subset of the plurality of glucose readings associated with a same time range within a total time range associated with the plurality of glucose readings;
determining a plurality of dynamic time warping (DTW) distances, each of the plurality of DTW distances comprising a DTW distance between the series of averages and one of the plurality of time series;
determining an average DTW distance based at least in part on the plurality of DTW distances; and
determining the gamma parameter based at least in part on the average DTW distance.

3. The computer-implemented method of claim 2, wherein determining the gamma parameter comprises setting the gamma parameter equal to either:
a first gamma value responsive to determining the average DTW distance is less than or equal to a DTW distance threshold; or
a multiple of the average DTW distance responsive to determining the average DTW distance exceeds the DTW distance threshold.

4. The computer-implemented method of claim 1, wherein the gamma parameter is a first gamma parameter, and the computer-implemented method further comprises:
determining at least two aligned series using a subset of the plurality of time series, a second gamma parameter, and an aggregate series; and
determining at least one aggregate uncertainty series using the at least two aligned series and the aggregate series.

5. The computer-implemented method of claim 4, wherein the aggregate series comprises the representative series.

6. The computer-implemented method of claim 4, wherein the second gamma parameter equals the gamma parameter.

7. The computer-implemented method of claim 4, wherein the subset of the plurality of time series comprises each of the plurality of time series.

8. The computer-implemented method of claim 4, wherein determining the at least two aligned series comprises:
determining an average alignment matrix based at least in part on the aggregate series, the second gamma parameter, and one time series of the plurality of time series; and
determining a series of weighted averages in which each of the series of weighted averages is:
determined using the one time series, and
weighted by a column of the average alignment matrix.

9. The computer-implemented method of claim 4, wherein determining the at least one aggregate uncertainty series comprises:
determining at least a first aligned percentile and a second aligned percentile of the at least two aligned series;

determining a difference between the first aligned percentile and the second aligned percentile; and adding the difference to the aggregate series.

10. The computer-implemented method of claim 9, wherein the first aligned percentile or the second aligned percentile is a fiftieth percentile.

11. The computer-implemented method of claim 4, wherein determining the at least one aggregate uncertainty series comprises:
   determining an aligned standard deviation series of the at least two aligned series; and
   determining an aggregate standard deviation series by either;
   adding the aligned standard deviation series to the aggregate series; or
   subtracting the aligned standard deviation series from the aggregate series.

12. The computer-implemented method of claim 1, wherein displaying the graphical display of the representative series via the user interface comprises:
   transmitting the representative series graphically to the user interface for display on the user interface, wherein the representative series is displayed on a plot, a first axis of the plot represents an amount of time relative to respective start times of the one or more time periods, and a second axis of the plot represents glucose concentration.

13. The computer-implemented method of claim 1, further comprising:
   identifying a feature in the representative series; and
   transmitting, to the user interface, a recommendation to engage in, refrain from, or modify an amount of a behavior at a time occurring within a threshold amount of time of the feature.

14. The computer-implemented method of claim 13, wherein the behavior comprises one or more of:
   engaging in physical activity;
   sleep;
   consuming carbohydrates; or
   administering a medication.

15. The computer-implemented method of claim 1, wherein the barycenter is a soft DTW barycenter.

16. The computer-implemented method of claim 1, wherein the plurality of time series share a common duration.

17. The computer-implemented method of claim 1, further comprising:
   generating the plurality of glucose readings using a glucose sensor.

18. One or more non-transitory computer-readable media storing processor-executable instructions that, when executed by one or more processors, cause the one or more processors to perform operations comprising:
   receiving a plurality of time series comprising a plurality of glucose readings respectively associated with a plurality of timestamps, the plurality of time series generated during one or more time periods;
   adaptively determining a gamma parameter based at least in part on (i) the plurality of glucose readings and (ii) the plurality of timestamps respectively associated with the plurality of glucose readings;
   determining a barycenter based at least in part on the plurality of time series and the gamma parameter;
   determining a representative series of the plurality of time series associated with the plurality of glucose readings by applying a smoothing function to the barycenter; and displaying a graphical display of the representative series via a user interface.

19. The one or more non-transitory computer-readable media of claim 18, wherein the processor-executable instructions further cause the one or more processors to perform operations comprising:
   determining a series of averages, wherein a first average of the series of averages is determined based at least in part on an average glucose reading determined using a subset of the plurality of glucose readings associated with a same time range within a total time range associated with the plurality of glucose readings;
   determining a plurality of dynamic time warping (DTW) distances, each of the plurality of DTW distances comprising a DTW distance between the series of averages and one of the plurality of time series;
   determining an average DTW distance based at least in part on the e plurality of DTW distances; and
   determining the gamma parameter bases at least in part on the average DTW distance.

20. The one or more non-transitory computer-readable media of claim 18, wherein the gamma parameter is a first gamma parameter, and wherein the processor-executable instructions further cause the one or more processors to perform operations comprising:
   determining at least two aligned series using a subset of the plurality of time series, a second gamma parameter, and an aggregate series; and
   determining at least one aggregate uncertainty series using the at least two aligned series and the aggregate series.

21. The one or more non-transitory computer-readable media of claim 18, wherein the processor-executable instructions further cause the one or more processors to perform operations comprising:
   generating the plurality of glucose readings using a glucose sensor.

22. A system comprising:
   one or more processors; and
   one or more memories storing processor-executable instructions that, when executed by the one or more processors, cause the one or more processors to perform operations comprising:
   receiving a plurality of time series comprising a plurality of glucose readings respectively associated with a plurality of timestamps, the plurality of time series generated during one or more time periods;
   adaptively determining a gamma parameter based at least in part on (i) the plurality of glucose readings and (ii) the plurality of timestamps respectively associated with the plurality of glucose readings;
   determining a barycenter based at least in part on the plurality of time series and the gamma parameter;
   determining a representative series of the plurality of time series associated with the plurality of glucose readings by applying a smoothing function to the barycenter; and
   displaying a graphical display of the representative series via a user interface.

23. The system of claim 22, further comprising a glucose sensor, the glucose sensor generating the plurality of glucose readings.

* * * * *

UNITED STATES PATENT AND TRADEMARK OFFICE
CERTIFICATE OF CORRECTION

Page 1 of 1

PATENT NO. : 12,353,683 B2
APPLICATION NO. : 17/754033
DATED : July 8, 2025
INVENTOR(S) : Javier Mosquera et al.

It is certified that error appears in the above-identified patent and that said Letters Patent is hereby corrected as shown below:

In the Claims

In Column 18, Claim 19, Line 19, delete "e plurality" and insert -- plurality --, therefor.

Signed and Sealed this
Seventh Day of October, 2025

John A. Squires
*Director of the United States Patent and Trademark Office*